(12) United States Patent
Dali et al.

(10) Patent No.: US 9,309,316 B2
(45) Date of Patent: Apr. 12, 2016

(54) STABLE SUBCUTANEOUS PROTEIN FORMULATIONS AND USES THEREOF

(71) Applicant: Bristol-Myers Squibb Company, Princeton, NJ (US)

(72) Inventors: Manisha D. Dali, Bridgewater, NJ (US); Charles E. Dahlheim, Lawrenceville, NJ (US); Sunita Borsadia, Plainsboro, NJ (US); Vijay H. Naringrekar, Princeton, NJ (US); Rajesh Babulal Gandhi, Plainsboro, NJ (US); Manoj Nerurkar, Kalyani Nagar (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/796,586

(22) Filed: Mar. 12, 2013

(65) Prior Publication Data

US 2013/0216541 A1    Aug. 22, 2013

Related U.S. Application Data

(62) Division of application No. 12/086,876, filed as application No. PCT/US2006/062297 on Dec. 19, 2006, now Pat. No. 8,476,239.

(60) Provisional application No. 60/752,150, filed on Dec. 20, 2005.

(51) Int. Cl.
  *C07K 14/705* (2006.01)
  *A61K 38/17* (2006.01)
  *C07K 16/46* (2006.01)
  *C07K 16/28* (2006.01)

(52) U.S. Cl.
  CPC ....... *C07K 16/2827* (2013.01); *C07K 14/70521* (2013.01); *C07K 2319/30* (2013.01)

(58) Field of Classification Search
  None
  See application file for complete search history.

(56) References Cited

U.S. PATENT DOCUMENTS

| | | | |
|---|---|---|---|
| 5,804,557 A * | 9/1998 | Cleland et al. | 514/11.3 |
| 5,844,095 A | 12/1998 | Linsley et al. | |
| 6,171,586 B1 | 1/2001 | Lam et al. | |
| 6,875,432 B2 | 4/2005 | Liu et al. | |
| 6,991,790 B1 | 1/2006 | Lam et al. | |
| 8,476,239 B2 | 7/2013 | Dali et al. | |
| 2002/0182211 A1 | 12/2002 | Peach et al. | |
| 2003/0083246 A1 | 5/2003 | Cohen et al. | |
| 2003/0138881 A1 | 7/2003 | Punnonen et al. | |
| 2004/0022787 A1 | 2/2004 | Cohen et al. | |
| 2004/0105889 A1 | 6/2004 | Ryde et al. | |
| 2005/0019859 A1 | 1/2005 | Schilling et al. | |
| 2005/0084933 A1 | 4/2005 | Schilling et al. | |
| 2005/0214278 A1 | 9/2005 | Kakuta et al. | |
| 2006/0099201 A1 * | 5/2006 | Andya et al. | 424/131.1 |
| 2007/0053871 A1 * | 3/2007 | Li et al. | 424/85.1 |
| 2009/0252749 A1 | 10/2009 | Leister et al. | |
| 2010/0166774 A1 | 7/2010 | Dali et al. | |

FOREIGN PATENT DOCUMENTS

| | | |
|---|---|---|
| AR | 254597 | 11/1996 |
| EP | 0 597 101 A1 | 7/1992 |
| EP | 1 475 101 A1 | 11/2004 |
| EP | 1 969 007 B1 | 8/2013 |
| EP | 1 962 886 B1 | 10/2013 |
| WO | WO9522347 | 8/1995 |
| WO | WO97/04801 | 2/1997 |
| WO | WO 97/28267 | 8/1997 |
| WO | WO 99/55310 | 11/1999 |
| WO | WO 99/64462 | 12/1999 |
| WO | WO02/02638 | 1/2002 |
| WO | WO 02/30463 A2 | 4/2002 |
| WO | WO02/058729 | 8/2002 |
| WO | WO03053465 A2 | 1/2003 |
| WO | WO03042344 A2 | 5/2003 |
| WO | WO03066102 A1 | 8/2003 |
| WO | WO 2004/016286 A2 | 2/2004 |
| WO | WO2004/058944 A2 | 7/2004 |
| WO | WO 2004/071439 A2 | 8/2004 |
| WO | WO2004/091658 | 10/2004 |
| WO | WO2005016266 A2 | 2/2005 |
| WO | WO 2005/072772 A1 | 8/2005 |
| WO | WO2006/044908 | 4/2006 |
| WO | WO 2006/065746 A2 | 6/2006 |
| WO | WO 2006/108035 A1 | 10/2006 |
| WO | WO 2007/076354 A2 | 7/2007 |

OTHER PUBLICATIONS

Sequence alignment, 2014, 1 page.*
U.S. Appl. No. 60/668,774, filed Apr. 6, 2005, Hagerty, et al.
Arakawa, et al., "Theory of Protein Solubility", Methods Enzymol., vol. 114, pp. 49-77 (1985).
Broach, James R., "Construction of High Copy Yeast Vectors Using 2-μm Circle Sequences", Methods Enzymol., vol. 101, pp. 307-325 (1983).
Clarke, et. al., "Selection Procedure for Isolation of Centromere DNAs from *Saccharomyces cerevisiae*", Methods Enzymol., vol. 101, pp. 300-307 (1983).
Cohen, et al., "Nonchromosomal Antibiotic Resistance in Bacteria: Genetic Transformation of *Escherichia coli* by R-Factor DNA", PNAS, vol. 69 (8), pp. 2110-2114 (1972).
Goeddel, et al., "Synthesis of human fibroblast interferon by *E. coli*", Nucleic Acids Res., vol. 8 (18), pp. 4057-4074 (1980).

(Continued)

*Primary Examiner* — Ilia Ouspenski
(74) *Attorney, Agent, or Firm* — Nickki Parlet

(57) ABSTRACT

The present invention relates generally to stable formulations comprising CTLA4Ig molecules, including lyophilized, and liquid formulations for administration via various routes including, for example, routes such as intravenous (IV) and subcutaneous (SC) for treating immune system diseases and tolerance induction.

44 Claims, 3 Drawing Sheets

(56) References Cited

OTHER PUBLICATIONS

Hess, et al., "Cooperation of Glycolytic Enzymes", J. Adv. Enzyme Reg., pp. 149-167 (1968).
Hitzeman, et al., "Isolation and Characterization of the Yeast-3-Phosphoglycerokinase Gene (PGK) by an Immunological Screening Technique", J. Biol. Chem., vol. 255 (24), pp. 12073-12080 (1980).
Holland, et al., "Isolation and Identification of Yeast Messenger Ribonucleic Acids Coding for Enolase, Glyceraldehyde-3-phosphate Dehydrogenase, and Phosphoglycerate Kinase", Biochem., pp. 4900-4907 (1978).
Jenkins, Terry W., "Three solutions of the protein solubility problem", Protein Science, vol. 7, pp. 376-382 (1998).
Karin, et al., "Human metallothionein genes—primary structure of the metallothionein-II gene and a related processed gene", Nature, vol. 299, pp. 797-802 (1982).
Kolhekar, et al., "Peptidylglycine α-Hydroxylating Monooxygenase: Active Site Residues, Disulfide Linkages, and a Two-Domain Model of the Catalytic Core", Biochem., vol. 36, pp. 10901-10909 (1997).
Sambrook et al. (eds.), "Molecular Cloning: A Laboratory Manual", 2nd Edition, Cold Spring Harbor Laboratory Press, (1989).
Schein, Catherine H., "Solubility as a Function of Protein Structure and Solvent Components", Biotechnology, vol. 8, pp. 308-317 (1990).
Shimatake, et al., "Purified λ regulatory protein cll positively activates promoters for lysogenic development", Nature, vol. 292, pp. 128-132 (1981).
Stinchcomb, et al., "Isolation and characterization of a yeast chromosomal replicator", Nature, vol. 282, pp. 39-43 (1979).
Toyama, et al., "Human chorionic gonadotropin α and human cytomegalovirus promoters are extremely active in the fission yeast Schizosaccharomyces pombe", FEBS Ltrs., vol. 268 (1), pp. 217-221 (1990).
Tschumper, et al., "Sequence of a yeast DNA fragment containing a chromosomal replicator and the TRP1 gene", Gene, vol. 10, pp. 157-166 (1980).
Urlaub, et al., "Effect of Gamma Rays at the Dihydrofolate Reductase Locus: Deletions and Inversions", Somatic Cell and Molec. Genetics, vol. 12 (6), pp. 555-566 (1986).
Van Der Merwe, et al., "CD80 (B7-1) Binds CD28 and CTLA-4 with a Low Affinity and Very Fast Kinetics", J. Exp. Med., vol. 185 (3), pp. 393-403 (1997).
Fiers, et al., "Complete nucleotide sequence of SV40 DNA", Nature, vol. 273, pp. 113-120 (1978).
Change, et al., "Expression in *Escherichia coli* of a Chemically Synthesized Gene for the Hormone Somatostatin", vol. 198, pp. 1056-1063 (1977).
Izutsu, Ken-ichi, "Stabilization of Protein Structure during Freeze-Drying", Cryobiology and Cryotechmology, vol. 49 (1), pp. 47-53 (2003).

Banga, Ajay K., "Therapeutic Peptides and Proteins Formulation, Processing, and Delivery Systems $2^{nd}$ Edition" Chapter 4, 2006, CRC/Taylor & Francis, 57 pages.
Carpenter, John F., et al., "Rational Design of Stable Protein Formulations Theory and Practice" Chapters 1, 3, 7 and 8, Kluwer Academic/Plenum Publishers, 2002, 109 pages.
Chamow, Steven M., et al., "Antibody Fusion Proteins", Wiley-Liss, 1999, pp. 232-233.
Chamow, Steven M., et al., "Immunoadhesins: principles and applications", TIBTECH, Feb. 1996, vol. 14, pp. 52-60.
Harris, Reed J., et al., "Commercial Manufacturing Scale Formulation and Analytical Characterization of Therapeutic Recombinant Antibodies", Drug Development Research, 2004, vol. 61, pp. 137-154.
Kendrick, Brent S., et al., "A transient expansion of the native state precedes aggregation of recombinant human interferon-γ", Proc. Natl. Acad. Sci., USA, Nov. 1998, vol. 95, pp. 14142-14146.
ADIS R&D Profile, "Omalizumab Anti-IgE monoclonal antibody E25, E25, Humanised anti-IgE MAb, IGE 025, Monoclonal antibody E25, Olizumab, Xolair, rhuMAb-E25", Biodrugs, 2002, vol. 16, No. 5, pp. 380-386.
Paborji, Mehdi, et al., "Chemical and Physical Stability of Chimeric L6, a Mouse-Human Monoclonal Antibody", Pharmaceutical Research, 1994, vol. 11, No. 5, 764-771.
Shin, Il-Seob, et al., "Cloning, expression and bioassay of canine CTLA4Ig", ScienceDirect, Veterinary Immunology and Immunopathology, 2007, vol. 118, pp. 12-18.
Shire, Steven J., et al., "Minireview Challenges in the Development of High Protein Concentration Formulations", Journal of Pharmaceutical Sciences, Jun. 2004, vol. 93, No. 6, pp. 1390-1402.
Srinvias, et al., "Pharmacokinetics of CTLA4Ig (BMS-188667), a Novel Immunosuppressive Agent, following Intravenous and Subcutaneous Administrations to Mice", Journal of Pharmaceutical Sciences, Dec. 1995, vol. 84, No. 12, pp. 1488-1489.
Timasheff, Serge N., "Control of Protein Stability and Reactions by Weakly Interacting Cosolvents: The Simplicity of the Complicated", Advances in Protein Chemistry, 1998, vol. 51, pp. 355-432.
Timasheff, Serge N., "Chapter 11 Solvent Stabilization of Protein Structure", Methods in Molecular Biology, 1995, vol. 40: Protein Stability and Folding: Theory and Practice, pp. 253-269.
Wang, Wei, "Instability, stabilization, and formulation of liquid protein pharmaceuticals", International Journal of Pharmaceutics, 1999, vol. 185, pp. 129-188.
International Preliminary Report on Patentability, date of issuance of this report: Jun. 24, 2008, 8 pages.
Summons to Oral Proceedings and Preliminary Opinion dated Aug. 5, 2015.

\* cited by examiner

FIG. 1

```
  1  AGCTTCACCA ATG GGT GTA CTG CTC ACA CAG AGG ACG CTG
                 M   G   V   L   L   T   Q   R   T   L
                 →  Oncostatin M Signal Sequence →
 41  CTC AGT CTG GTC CTT GCA CTC CTG TTT CCA AGC ATG GCG
     L   S   L   V   L   A   L   L   F   P   S   M   A 80  AGC ATG GCA ATG CAC GTG GCC CAG CCT GCT GTG GTA CTG
     S   M   A   M   H   V   A   Q   P   A   V   V   L
                 →  Human CTLA4 →
119  GCC AGC AGC CGA GGC ATC GCC AGC TTT GTG TGT GAG TAT
     A   S   S   R   G   I   A   S   F   V   C   E   Y 158  GCA TCT CCA GGC AAA GCC ACT GAG GTC CGG GTG ACA GTG
     A   S   P   G   K   A   T   E   V   R   V   T   V 197  CTT CGG CAG GCT GAC AGC CAG GTG ACT GAA GTC TGT GCG
     L   R   Q   A   D   S   Q   V   T   E   V   C   A 236  GCA ACC TAC ATG ATG GGG AAT GAG TTG ACC TTC CTA GAT
     A   T   Y   M   M   G   N   E   L   T   F   L   D 275  GAT TCC ATC TGC ACG GGC ACC TCC AGT GGA AAT CAA GTG
     D   S   I   C   T   G   T   S   S   G   N   Q   V 314  AAC CTC ACT ATC CAA GGA CTG AGG GCC ATG GAC ACG GGA
     N   L   T   I   Q   G   L   R   A   M   D   T   G 353  CTC TAC ATC TGC AAG GTG GAG CTC ATG TAC CCA CCG CCA
     L   Y   I   C   K   V   E   L   M   Y   P   P   P 392  TAC TAC CTG GGC ATA GGC AAC GGA ACC CAG ATT TAT GTA
     Y   Y   L   G   I   G   N   G   T   Q   I   Y   V 431  ATT GAT CCA GAA CCG TGC CCA GAT TCT GAT CAG GAG CCC
     I   D   P   E   P   C   P   D   S   D   Q   E   P
                                                 →
470  AAA TCT TCT GAC AAA ACT CAC ACA TCC CCA CCG TCC CCA
     K   S   S*  D   K   T   H   T   S*  P   P   S*  P
     Human IgG₁ Hinge →
509  GCA CCT GAA CTC CTG GGG GGA TCG TCA GTC TTC CTC TTC
     A   P   E   L   L   G   G   S*  S   V   F   L   F
     →  Human IgG₁ C_H2 Domain →
548  CCC CCA AAA CCC AAG GAC ACC CTC ATG ATC TCC CGG ACC
     P   P   K   P   K   D   T   L   M   I   S   R   T
```

FIG. 1 (continued)

```
587  CCT GAG GTC ACA TGC GTG GTG GTG GAC GTG AGC CAC GAA
      P   E   V   T   C   V   V   V   D   V   S   H   E

626  GAC CCT GAG GTC AAG TTC AAC TGG TAC GTG GAC GGC GTG
      D   P   E   V   K   F   N   W   Y   V   D   G   V

665  GAG GTG CAT AAT GCC AAG ACA AAG CCG CGG GAG GAG CAG
      E   V   H   N   A   K   T   K   P   R   E   E   Q

704  TAC AAC AGC ACG TAC CGT GTG GTC AGC GTC CTC ACC GTC
      Y   N   S   T   Y   R   V   V   S   V   L   T   V

743  CTG CAC CAG GAC TGG CTG AAT GGC AAG GAG TAC AAG TGC
      L   H   Q   D   W   L   N   G   K   E   Y   K   C

782  AAG GTC TCC AAC AAA GCC CTC CCA GCC CCC ATC GAG AAA
      K   V   S   N   K   A   L   P   A   P   I   E   K

821  ACC ATC TCC AAA GCC AAA|GGG CAG CCC CGA GAA CCA CAG
      T   I   S   K   A   K |  G   Q   P   R   E   P   Q
                             └─> Human IgG₁ C_H3 Domain →

860  GTG TAC ACC CTG CCC CCA TCC CGG GAT GAG CTG ACC AAG
      V   Y   T   L   P   P   S   R   D   E   L   T   K

899  AAC CAG GTC AGC CTG ACC TGC CTG GTC AAA GGC TTC TAT
      N   Q   V   S   L   T   C   L   V   K   G   F   Y

938  CCC AGC GAC ATC GCC GTG GAG TGG GAG AGC AAT GGG CAG
      P   S   D   I   A   V   E   W   E   S   N   G   Q

977  CCG GAG AAC AAC TAC AAG ACC ACG CCT CCC GTG CTG GAC
      P   E   N   N   Y   K   T   T   P   P   V   L   D

1016 TCC GAC GGC TCC TTC TTC CTC TAC AGC AAG CTC ACC GTG
      S   D   G   S   F   F   L   Y   S   K   L   T   V

1055 GAC AAG AGC AGG TGG CAG CAG GGG AAC GTC TTC TCA TGC
      D   K   S   R   W   Q   Q   G   N   V   F   S   C

1094 TCC GTG ATG CAT GAG GCT CTG CAC AAC CAC TAC ACG CAG
      S   V   M   H   E   A   L   H   N   H   Y   T   Q

1133 AAG AGC CTC TCC CTG TCT CCG GGT AAA TGA GTGCGACG
      K   S   L   S   L   S   P   G   K   -

1172 GCCGGCAAGC CCCGCTCCCC GGGCTCTCGC GGTCGCAC GAGGATGCTT
1222 CTAGA
```

FIG. 2

```
ATGGGTGTACTGCTCACACAGAGGACGCTGCTCAGTCTGGTCCTTGCACTCCTGTTTCCA        -19
M--G--V--L--L--T--Q--R--T--L--L--S--L--V--L--A--L--F--P--          -7

AGCATGGCGAGCATGGCAATGCACGTGGCCCAGCCTGCTGTGGTACTGGCCAGCAGCCGA        +42
S--M--A--S--M--A--M--H--V--A--Q--P--A--V--V--L--A--S--S--R--       +14
                                 +1

GGCATCGCTAGCTTTGTGTGTGAGTATGCATCTCCAGGCAAATATACTGAGGTCCGGGTG       +102
G--I--A--S--F--V--C--E--Y--A--S--P--G--K--Y--T--E--V--R--V--       +34

ACAGTGCTTCGGCAGGCTGACAGCCAGGTGACTGAAGTCTGTGCGGCAACCTACATGATG       +162
T--V--L--R--Q--A--D--S--Q--V--T--E--V--C--A--A--T--Y--M--M--       +54

GGGAATGAGTTGACCTTCCTAGATGATTCCATCTGCACGGGCACCTCCAGTGGAAATCAA       +222
G--N--E--L--T--F--L--D--D--S--I--C--T--G--T--S--S--G--N--Q--       +74

GTGAACCTCACTATCCAAGGACTGAGGGCCATGGACACGGGACTCTACATCTGCAAGGTG       +282
V--N--L--T--I--Q--G--L--R--A--M--D--T--G--L--Y--I--C--K--V--       +94

GAGCTCATGTACCCACCGCCATACTACGAGGGCATAGGCAACGGAACCCAGATTTATGTA       +342
E--L--M--Y--P--P--P--Y--Y--E--G--I--G--N--G--T--Q--I--Y--V--       +114

ATTGATCCAGAACCGTGCCCAGATTCTGATCAGGAGCCCAAATCTTCTGACAAAACTCAC       +402
I--D--P--E--P--C--P--D--S--D--Q--E--P--K--S--S--D--K--T--H--       +134

ACATCCCCACCGTCCCCAGCACCTGAACTCCTGGGGGGATCGTCAGTGTTCCTCTTCCCC       +462
T--S--P--P--S--P--A--P--E--L--L--G--G--S--S--V--F--L--F--P--       +154

CCAAAACCCAAGGACACCCTCATGATCTCCCGGACCCCTGAGGTCACATGCGTGGTGGTG       +522
P--K--P--K--D--T--L--M--I--S--R--T--P--E--V--T--C--V--V--V--       +174

GACGTGAGCCACGAAGACCCTGAGGTCAAGTTCAACTGGTACGTGGACGGCGTGGAGGTG       +582
D--V--S--H--E--D--P--E--V--K--F--N--W--Y--V--D--G--V--E--V--       +194

CATAATGCCAAGACAAAGCCGCGGGAGGAGCAGTACAACAGCACGTACCGTGTGGTCAGC       +642
H--N--A--K--T--K--P--R--E--E--Q--Y--N--S--T--Y--R--V--V--S--       +214

GTCCTCACCGTCCTGCACCAGGACTGGCTGAATGGCAAGGAGTACAAGTGCAAGGTCTCC       +702
V--L--T--V--L--H--Q--D--W--L--N--G--K--E--Y--K--C--K--V--S--       +234

AACAAAGCCCTCCCAGCCCCCATCGAGAAAACCATCTCCAAAGCCAAAGGGCAGCCCCGA       +762
N--K--A--L--P--A--P--I--E--K--T--I--S--K--A--K--G--Q--P--R--       +254

GAACCACAGGTGTACACCCTGCCCCCATCCCGGGATGAGCTGACCAAGAACCAGGTCAGC       +822
E--P--Q--V--Y--T--L--P--P--S--R--D--E--L--T--K--N--Q--V--S--       +274

CTGACCTGCCTGGTCAAAGGCTTCTATCCCAGCGACATCGCCGTGGAGTGGGAGAGCAAT       +882
L--T--C--L--V--K--G--F--Y--P--S--D--I--A--V--E--W--E--S--N--       +294

GGGCAGCCGGAGAACAACTACAAGACCACGCCTCCCGTGCTGGACTCCGACGGCTCCTTC       +942
G--Q--P--E--N--N--Y--K--T--T--P--P--V--L--D--S--D--G--S--F--       +314

TTCCTCTACAGCAAGCTCACCGTGGACAAGAGCAGGTGGCAGCAGGGGAACGTCTTCTCA      +1002
F--L--Y--S--K--L--T--V--D--K--S--R--W--Q--Q--G--N--V--F--S--       +334

TGCTCCGTGATGCATGAGGCTCTGCACAACCACTACACGCAGAAGAGCCTCTCCCTGTCT      +1062
C--S--V--M--H--E--A--L--H--N--H--Y--T--Q--K--S--L--S--L--S--       +354

CCGGGTAAATGA
P--G--K--*
```

STABLE SUBCUTANEOUS PROTEIN FORMULATIONS AND USES THEREOF

The present patent application is a divisional application of U.S. Ser. No. 12/086,876 filed Dec. 19, 2006, now allowed, which claims the priority of provisional application U.S. Ser. No. 60/752,150, filed on Dec. 20, 2005, the contents of which are hereby incorporated by reference in their entirety into this application All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

FIELD OF THE INVENTION

The present invention relates generally to stable formulations comprising CTLA4Ig molecules, including lyophilized, and liquid formulations for administration via various routes including, for example, routes such as intravenous (IV) and subcutaneous (SC).

BACKGROUND OF THE INVENTION

Over the past two decades, recombinant DNA technology has led to the commercialization of many protein therapeutics. The most conventional route of delivery for protein drugs has been intravenous (IV) administration because of poor bioavailability by most other routes, greater control during clinical administration, and faster pharmaceutical development. For products that require frequent and chronic administration, the alternate subcutaneous (SC) route of delivery is more appealing. When coupled with pre-filled syringe and autoinjector device technology, SC delivery allows for home administration and improved compliance of administration.

Treatments with high doses of more than 1 mg/kg or 100 mg per dose often require development of formulations at concentrations exceeding 100 mg/ml because of the small volume (<1.5 ml) that can be given by the SC routes. For proteins that have a propensity to aggregate at the higher concentrations, achieving such high concentration formulations is a developmental challenge. Even for the IV delivery route, where large volumes can be administered, protein concentrations of tens of milligrams per milliliter may be needed for high dosing regimens and this may pose stability challenges for some proteins.

The principles governing protein solubility are more complicated than those for small synthetic molecules, and thus overcoming the protein solubility issue takes different strategies. Operationally, solubility for proteins could be described by the maximum amount of protein in the presence of co-solutes whereby the solution remains visibly clear (i.e., does not show protein precipitates, crystals, or gels). The dependence of protein solubility on ionic strength, salt form, pH, temperature, and certain excipients has been mechanistically explained by changes in bulk water surface tension and protein binding to water and ions versus self-association by Arakawa et al in *Theory of protein solubility*, Methods of Enzymology, 114:49-77, 1985; Schein in *Solubility as a function of protein structure and solvent components*, BioTechnology 8(4):308-317, 1990; Jenkins in *Three solutions of the protein solubility problem*, Protein Science 7(2):376-382, 1998; and others. Binding of proteins to specific excipients or salts influences solubility through changes in protein conformation or masking of certain amino acids involved in self-interaction. Proteins are also preferentially hydrated (and stabilized as more compact conformations) by certain salts, amino acids, and sugars, leading to their altered solubility.

Aggregation which requires bi-molecular collision is expected to be the primary degradation pathway in protein solutions. The relationship of concentration to aggregate formation depends on the size of aggregates as well as the mechanism of association. Protein aggregation may result in covalent (e.g., disulfide-linked) or non-covalent (reversible or irreversible) association. Irreversible aggregation by non-covalent association generally occurs via hydrophobic regions exposed by thermal, mechanical, or chemical processes that alter a protein's native conformation. Protein aggregation may impact protein activity, pharmacokinetics and safety, e.g., due to immunogenicity.

A typical approach to minimize aggregation, is to restrict the mobility of proteins in order to reduce the number of collisions. Lyophilization with appropriate excipients may improve protein stability against aggregation by decreasing protein mobility and by restricting conformational flexibility with the added benefit of minimizing hydrolytic reactions consequent to removal of water. The addition of appropriate excipients, including lyoprotectants, can prevent the formation of aggregates during the lyophilization process as well as during storage of the final product. A key parameter for effective protection is the molar ratio of the lyoprotectant to the protein. Generally molar ratios of 300:1 or greater are required to provide suitable stability, especially for room temperature storage. Such ratios can also, however, lead to an undesirable increase in viscosity.

Lyophilization allows for designing a formulation with appropriate stability and tonicity. Although isotonicity is not necessarily required for SC administration, it may be desirable for minimizing pain upon administration. Isotonicity of a lyophile is difficult to achieve because both the protein and the excipients are concentrated during the reconstitution process. Excipient:protein molar ratios of 500:1 will result in hypertonic preparations if the final protein concentration is targeted for >100 mg/ml. If the desire is to achieve an isotonic formulation, then a choice of lower molar ratio of excipient: protein will result in a potentially less stable formulation.

Determining the highest protein concentration achievable remains an empirical exercise due to the labile nature of protein conformation and the propensity to interact with itself, with surfaces, and with specific solutes.

Examples of subjects who may benefit from SC formulations are those that have conditions that require frequent and chronic administration such as subjects with the immune system disease rheumatoid arthritis and immune disorders associated with graft transplantation. Commercially available protein drug products for the treatment of rheumatoid arthritis include HUMIRA®, ENBREL® and REMICADE®.

HUMIRA® (Abbott) is supplied in single-use, 1 ml prefilled glass syringes as a sterile, preservative-free solution for subcutaneous administration. The solution of HUMIRA® is clear and colorless, with a pH of about 5.2. Each syringe delivers 0.8 ml (40 mg) of drug product. Each 0.8 ml of HUMIRA® contains 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80 and Water for Injection, USP. Sodium hydroxide added as necessary to adjust pH.

ENBREL® (Amgen) is supplied in a single-use pre-filled 1 ml syringe as a sterile, preservative-free solution for subcutaneous injection. The solution of ENBREL® is clear and colorless and is formulated at pH 6.3±0.2. Each ENBREL® single-use prefilled syringe contains 0.98 ml of a 50 mg/ml solution of etanercept with 10 mg/ml sucrose, 5.8 mg/ml sodium chloride, 5.3 mg/ml L-arginine hydrochloride, 2.6 mg/ml sodium phosphate monobasic monohydrate and 0.9 mg/ml sodium phosphate dibasic anhydrous. Administration of one 50 mg/ml prefilled syringe of ENBREL® provides a dose equivalent to two 25 mg vials of lyophilized ENBREL®, when vials are reconstituted and administered as recommended. ENBREL® multiple-use vial contains sterile, white, preservative-free, lyophilized powder. Reconstitution with 1 ml of the supplied Sterile Bacteriostatic Water for Injection (BWFI), USP (containing 0.9% benzyl alcohol) yields a multiple-use, clear, and colorless solution with a pH of 7.4±0.3 containing 25 mg etanereept, 40 mg mannitol, 10 mg sucrose, and 1.2 mg tromethamine.

REMICADE® (Centocor) is supplied as a sterile, white, lyophilized powder for intravenous infusion. Following reconstitution with 10 ml of Sterile Water for Injection, USP, the resulting pH is approximately 7.2. Each single-use vial contains 100 mg infliximab, 500 mg sucrose, 0.5 mg polysorbate 80, 2.2 mg monobasic sodium phosphate, monohydrate, and 6.1 mg dibasic sodium phosphate, dihydrate. No preservatives are present.

Commercially available protein drug products for the treatment of immune disorders associated with graft transplantation include SIMULECT®, and ZENAPAX®.

The drug product, SIMULECT® (Novartis), is a sterile lyophilisate which is available in 6 ml colorless glass vials and is available in 10 mg and 20 mg strengths. Each 10-mg vial contains 10 mg basiliximab, 3.61 mg monobasic potassium phosphate, 0.50 mg disodium hydrogen phosphate (anhydrous), 0.80 mg sodium chloride, 10 mg sucrose, 40 mg mannitol and 20 mg glycine, to be reconstituted in 2.5 ml of Sterile Water for Injection, USP. Each 20-mg vial contains 20 mg basiliximab, 7.21 mg monobasic potassium phosphate, 0.99 mg disodium hydrogen phosphate (anhydrous), 1.61 mg sodium chloride, 20 mg sucrose, 80 mg mannitol and 40 mg glycine, to be reconstituted in 5 ml of Sterile Water for Injection, USP. No preservatives are added.

ZENAPAX® (Roche Laboratories), 25 mg/5 ml, is supplied as a clear, sterile, colorless concentrate for further dilution and intravenous administration. Each milliliter of ZENAPAX® contains 5 mg of daclizumab and 3.6 mg sodium phosphate monobasic monohydrate, 11 mg sodium phosphate dibasic heptahydrate, 4.6 mg sodium chloride, 0.2 mg polysorbate 80, and may contain hydrochloric acid or sodium hydroxide to adjust the pH to 6.9. No preservatives are added CTLA4Ig molecules interfere with T cell costimulation by inhibiting the CD28-B7 interaction. Therefore, CTLA4Ig molecules can provide a therapeutic use for immune system diseases, such as rheumatoid arthritis and immune disorders associated with graft transplantation.

There is a need for a stable, effective convenient formulations comprising CTLA4Ig molecules for treatment of immune system disorders.

SUMMARY OF THE INVENTION

The present invention provides formulations for treating immune system diseases, by administering to a subject CTLA4Ig molecules, which bind to B7 molecules on B7-positive cells, thereby inhibiting endogenous B7 molecules from binding CTLA4 and/or CD28 on T-cells.

The lyophilized formulation of the invention comprises the CTLA4Ig molecule in a weight ratio of at least 1:2 protein to lyoprotectant. The lyoprotectant is preferably sugar, more preferably disaccharides, most preferably sucrose or maltose. The lyophilized formulation may also comprise one or more of the components selected from the list consisting of buffering agents, surfactants, bulking agents and preservatives.

In certain embodiments, the amount of sucrose or maltose useful for stabilization of the lyophilized drug product is in a weight ratio of at least 1:2 protein to sucrose or maltose, preferably in a weight ratio of from 1:2 to 1:5 protein to sucrose or maltose, more preferably in a weight ratio of about 1:2 protein to maltose or sucrose.

The subcutaneous (SC) formulation of the invention comprises the CTLA4Ig molecule at a protein concentration of at least 100 mg/ml in combination with a sugar at stabilizing levels, preferably a protein concentration of at least 125 mg/ml in combination with a sugar at stabilizing levels, in an aqueous carrier. The sugar is preferably in a weight ratio of at least 1:1.1 protein to sugar. The stabilizer is preferably employed in an amount no greater than that which may result in a viscosity undesirable or unsuitable for administration via SC syringe. The sugar is preferably disaccharides, most preferably sucrose. The SC formulation may also comprise one or more of the components selected from the list consisting of buffering agents, surfactants, and preservatives.

In certain embodiments, the amount of sucrose useful for stabilization of the CTLA4Ig molecule SC drug product is in a weight ratio of at least 1:1 protein to sucrose, preferably in a weight ratio of from 1:1.3 to 1:5 protein to sucrose, more preferably in a weight ratio of about 1:1.4 protein to sucrose.

The liquid formulation of the invention comprises the CTLA4Ig molecule at a protein concentration of at least 20 mg/ml in combination with a sugar at stabilizing levels, preferably at least 25 mg/ml in combination with a sugar at stabilizing level in an aqueous carrier. Preferably the sugar is in a weight ratio of at least 1:1 protein to sugar. The sugar is preferably disaccharides, most preferably sucrose. The liquid formulation may also comprise one or more of the components selected from the list consisting of buffering agents, surfactants, and preservatives.

In certain embodiments, the amount of sucrose useful for stabilization of the liquid drug product is in a weight ratio of at least 1:1 protein to sucrose, preferably in a weight ratio of from 1:2 to 1:10 protein to sucrose, more preferably in a weight ratio of about 1:2 protein to sucrose.

In another embodiment of the invention, an article of manufacture is provided which contains the drug product and preferably provides instructions for its use.

The present invention further provides methods for treating immune system diseases and tolerance induction by administering the CTLA4Ig molecule formulations of the invention.

BRIEF DESCRIPTION OF THE DRAWINGS

FIG. 1 presents the nucleotide sequence (SEQ ID NO:1) of a portion of an expression cassette for a CTLA4-Ig molecule. Also shown is the amino acid sequence (SEQ ID NO:2) encoded by the nucleic acid. CTLA4-Ig molecules that can be produced from this expression cassette include molecules having the amino acid sequence of residues: (i) 26-383 of SEQ ID NO:2, (ii) 26-382 of SEQ ID NO:2, (iii) 27-383 of SEQ ID NO:2, or (iv) 26-382 of SEQ ID NO:2, or optionally (v) 25-382 of SEQ ID NO:2, or (vi) 25-383 of SEQ ID NO:2. The expression cassette comprises the following regions: (a) an Oncostatin M signal sequence (nucleotides 11-88 of SEQ ID NO: 1; amino acids 1-26 of SEQ ID NO:2); (b) an extracellular domain of human CTLA4 (nucleotides 89-463 of SEQ ID NO:1; amino acids 27-151 of SEQ ID NO:2); (c) a modified portion of the human IgG1 constant region (nucleotides 464-1159 of SEQ ID NO: 1; amino acids 152-383 of SEQ ID NO:2), including a modified hinge region (nucleotides 464-508 of SEQ ID NO:1; amino acids 152-166 of SEQ ID NO:2), a modified human IgG1 CH2 domain (nucleotides 509-838 of SEQ ID NO:1; amino acids 167-276 of SEQ ID NO:2), and a human IgG1 CH3 domain (nucleotides 839-1159 of SEQ ID NO:1; amino acids 277-383 of SEQ ID NO:2).

FIG. 2 depicts a nucleotide (SEQ ID NO:3) and amino acid (SEQ ID NO:4) sequence of CTLA4-L104EA29Y-Ig (also know as "L104EA29YIg" and "LEA29Y") comprising a signal peptide; a mutated extracellular domain of CTLA4 starting at methionine at position +1 and ending at aspartic acid at position +124, or starting at alanine at position −1 and ending at aspartic acid at position +124; and an Ig region. SEQ ID NO: 3 and 4 depict a nucleotide and amino acid sequence, respectively, of L104EA29YIg comprising a signal peptide; a mutated extracellular domain of CTLA4 starting at methionine at position +27 and ending at aspartic acid at position +150, or starting at alanine at position +26 and ending at aspartic acid at position +150; and an Ig region. L104EA29YIg can have the amino acid sequence of residues: (i) 26-383 of SEQ ID NO:4, (ii) 26-382 of SEQ ID NO:4; (iii) 27-383 of SEQ ID NO:4 or (iv) 27-382 of SEQ ID NO:4, or optionally (v) 25-382 of SEQ ID NO:4, or (vi) 25-383 of SEQ ID NO:4.

DETAILED DESCRIPTION OF THE INVENTION

As utilized herein:

A "stable" formulation or drug product is one in which the CTLA4Ig molecule therein essentially retains its physical and chemical stability and integrity upon storage. Stability of the CTLA4Ig molecule formulations can be measured at selected temperatures after selected time periods. For example, an increase in aggregate formation following lyophilization and storage is an indicator for instability of a lyophilized. CTLA4Ig molecule formulation. In addition to aggregate formation, retention of original clarity, color and odor throughout shelf life are indicators utilized to monitor stability of CTLA4Ig molecule solutions. HMW species are multimers (i.e. tetramers, hexamers, etc), which have a higher molecular weight than CTLA4Ig molecule dimers. Typically a "stable" drug product may be one wherein the increase in aggregation, as measured by an increase in the percentage of high molecular weight species (% HMW), is less than about 5% and preferably less than about 3%, when the formulation is stored at 2-8° C. for one year. Preferably, the manufactured drug product comprises less than about 25% HMW species, preferably less than about 15% HMW species, more preferably less than about 10% HMW species, most preferred less than about 5% HMW species.

The monomer, dimer and HMW species of CTLA4Ig molecule may be separated by size exclusion chromatography (SEC). SEC separates molecules based on the molecular size. Separation is achieved by the differential molecular exclusion or inclusion as the molecules migrate along the length of the column. Thus, resolution increases as a function of column length. CTLA4Ig molecule samples may be separated using a 2695 Alliance HPLC (Waters, Milford, Mass.) equipped with TSK Gel® G3000SWXL (300 mm×7.8 mm) and TSK Gel® G3000SWXL (40 mm×6.0 mm) columns (Tosoh Bioscience, Montgomery, Pa.) in tandem. Samples at 10 mg/ml (20 µl aliquot) are separated using a mobile phase consisting of 0.2 M $KH_2PO_4$, 0.9% NaCl, pH 6.8, at a flow rate of 1.0 ml/min. Samples are monitored at an absorbance of 280 nm using Water's 2487 Dual Wavelength detector. Using this system, the HMW species has a retention time of 7.5 min±1.0 min. Each peak is integrated for area under the peak. The % HMW species calculated by dividing the HMW peak area by the total peak area.

A "reconstituted" formulation is one which has been prepared by dissolving a lyophilized formulation in an aqueous carrier such that the CTLA4Ig molecule is dissolved in the reconstituted formulation. The reconstituted formulation is suitable for intravenous administration (IV) to a patient in need thereof.

An "isotonic" formulation is one which has essentially the same osmotic pressure as human blood. Isotonic formulations will generally have an osmotic pressure from about 250 to 350 mOsmol/KgH2O. The term "hypertonic" is used to describe a formulation with an osmotic pressure above that of human blood. Isotonicity can be measured using a vapor pressure or ice-freezing type osmometer, for example.

The term "buffering agent" refers to one or more components that when added to an aqueous solution is able to protect the solution against variations in pH when adding acid or alkali, or upon dilution with a solvent. In addition to phosphate buffers, there can be used glycinate, carbonate, citrate buffers and the like, in which case, sodium, potassium or ammonium ions can serve as counterion.

An "acid" is a substance that yields hydrogen ions in aqueous solution. A "pharmaceutically acceptable acid" includes inorganic and organic acids which are non toxic at the concentration and manner in which they are formulated.

A "base" is a substance that yields hydroxyl ions in aqueous solution. "Pharmaceutically acceptable bases" include inorganic and organic bases which are non-toxic at the concentration and manner in which they are formulated.

A "lyoprotectant" is a molecule which, when combined with a protein of interest, prevents or reduces chemical and/or physical instability of the protein upon lyophilization and subsequent storage.

A "preservative" is an agent that reduces bacterial action and may be optionally added to the formulations herein. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3pentanol, and m-cresol.

A "surfactant" is a surface active molecule containing both a hydrophobic portion (e.g., alkyl chain) and a hydrophilic portion (e.g., carboxyl and carboxylate groups). Surfactant may be added to the formulations of the invention. Surfactants suitable for use in the formulations of the present invention include, but are not limited to, polysorbates (e.g. polysorbates 20 or 80); poloxamers (e.g. poloxamer 188); sorbitan esters and derivatives; Triton; sodium laurel sulfate; sodium octyl glycoside; lauryl-, myristyl-, linoleyl-, or stearyl-sulfobetadine; lauryl-, linoleyl- or stearyl-sarcosine; linoleyl-, myristyl-, or cetyl-betaine; lauramidopropyl-cocamidopropyl-, linoleamidopropyl-, myristamidopropyl-, palmidopropyl-, or isostearamidopropylbetaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethylene glycol, polypropyl glycol, and copolymers of ethylene and propylene glycol (e.g., Pluronics, PF68 etc.).

A "drug substance" refers to the starting material utilized in formulation of the final drug product. Typical CTLA4Ig drug substance composition comprises a protein concentration from 20 mg/ml to 60 mg/ml, pH from 7 to 8 and % HMW species of <5%.

A "formulated bulk solution" refers to the final formulation prior to filling of the container such as the formulated solution prior to filling the vials for lyophilization, or the formulated solution prior to filling the syringe for SC injection.

A "drug product" refers to the final formulation packaged in a container which may be reconstituted before use, such as with a lyophilized drug product; diluted further before use, such as with a liquid drug product; or utilized as is, such as with a SC solution drug product.

The terms "CTLA4-Ig" or "CTLA4-Ig molecule" or "CTLA4Ig molecule" are used interchangeably, and refer to a protein molecule that comprises at least a polypeptide having a CTLA4 extracellular domain or portion thereof and an immunoglobulin constant region or portion thereof. The extracellular domain and the immunoglobulin constant region can be wild-type, or mutant or modified, and mammalian, including human or mouse. The polypeptide can further comprise additional protein domains. A CTLA4-Ig molecule can also refer to multimer forms of the polypeptide, such as dimers, tetramers, and hexamers. A CTLA4-Ig molecule also is capable of binding to CD80 and/or CD86.

The term "B7-1" refers to CD80; the term "B7-2" refers CD86; and the term "B7" refers to both B7-1 and B7-2 (CD80 and CD86). The term "B7-1-Ig" or "B7-1Ig" refers to CD80-Ig; the term "B7-2-Ig" or "B7-2Ig" refers CD86-Ig.

In one embodiment, "CTLA4Ig" refers to a protein molecule having the amino acid sequence of residues: (i) 26-383 of SEQ ID NO:2, (ii) 26-382 of SEQ ID NO:2; (iii) 27-383 of SEQ ID NO:2, or (iv) 27-382 of SEQ ID NO:2, or optionally (v) 25-382 of SEQ ID NO:2, or (vi) 25-383 of SEQ ID NO:2. In monomeric form these proteins can be referred to herein as "SEQ ID NO:2 monomers," or monomers "having a SEQ ID NO:2 sequence". These SEQ ID NO:2 monomers can dimerize, such that dimer combinations can include, for example: (i) and (i); (i) and (ii); (i) and (iii); (i) and (iv); (i) and (v); (i) and (vi); (ii) and (ii); (ii) and (iii); (ii) and (iv); (ii) and (v); (ii) and (vi); (iii) and (iii); (iii) and (iv); (iii) and (v); (iii) and (vi); (iv) and (iv); (iv) and (v); (iv) and (vi); (v) and (v); (v) and (vi); and, (vi) and (vi). These different dimer combinations can also associate with each other to form tetramer CTLA4Ig molecules. These monomers, dimers, tetramers and other multimers can be referred to herein as "SEQ ID NO:2 proteins" or proteins "having a SEQ ID NO:2 sequence". (DNA encoding CTLA4Ig as shown in SEQ ID NO:2 was deposited on May 31, 1991 with the American Type Culture Collection (ATCC), 10801 University Blvd., Manassas, Va. 20110-2209 under the provisions of the Budapest Treaty, and has been accorded ATCC accession number ATCC 68629; a Chinese Hamster Ovary (CHO) cell line expressing CTLA4Ig as shown in SEQ ID NO:2 was deposited on May 31, 1991 with ATCC identification number CRL-10762). As utilized herein "Abatacept" refers to SEQ ID NO:2 proteins.

In one embodiment, CTLA4-L104EA29Y-Ig (sometimes known as "LEA29Y" or "L104EA29Y") is a genetically engineered fusion protein similar in structure to CTAL4-Ig molecule as shown in SEQ ID NO: 1. L104EA29Y-Ig has the functional extracellular binding domain of modified human CTLA4 and the Fc domain of human immunoglobulin of the IgG1 class. Two amino acid modifications, leucine to glutamic acid at position 104 (L104E), which is position 130 of SEQ ID NO:2, and alanine to tyrosine at position 29 (A29Y), which is position 55 of SEQ ID NO:2, were made in the B7 binding region of the CTLA4 domain to generate L104EA29Y. SEQ ID NOS: 3 and 4 depict a nucleotide and amino acid sequence, respectively, of L104EA29YIg comprising a signal peptide; a mutated extracellular domain of CTLA4 starting at methionine at position +27 and ending at aspartic acid at position +150, or starting at alanine at position +26 and ending at aspartic acid at position +150; and an Ig region. DNA encoding L104EA29Y-Ig was deposited on Jun. 20, 2000, with the American Type Culture Collection (ATCC) under the provisions of the Budapest Treaty. It has been accorded ATCC accession number PTA-2104. L104EA29Y-Ig is farther described in U.S. Pat. No. 7,094,874, issued on Aug. 22, 2006, and in WO 01/923337 A2, which are incorporated by reference herein in their entireties.

Expression of L104EA29YIg in mammalian cells can result in the production of N- and C-terminal variants, such that the proteins produced can have the amino acid sequence of residues: (i) 26-383 of SEQ ID NO:4, (ii) 26-382 of SEQ ID NO:4; (iii) 27-383 of SEQ ID NO:4 or (iv) 27-382 of SEQ ID NO:4, or optionally (v) 25-382 of SEQ ID NO:4, or (vi) 25-383 of SEQ ID NO:4. In monomeric form these proteins can be referred to herein as "SEQ ID NO:4 monomers," or monomers "having a SEQ ID NO:4 sequence. These proteins can dimerize, such that dimer combinations can include, for example: (i) and (i); (i) and (ii); (i) and (iii); (i) and (iv); (i) and (v); (i) and (vi); (ii) and (ii); (ii) and (iii); (ii) and (iv); (ii) and (v); (ii) and (vi); (iii) and (iii); (iii) and (iv); (iii) and (v); (iii) and (vi); (iv) and (iv); (iv) and (v); (iv) and (vi); (v) and (v); (v) and (vi); and, (vi) and (vi)." These different dimer combinations can also associate with each other to form tetramer L104EA29YIg molecules. These monomers, dimers, tetramers and other multimers can be referred to herein as "SEQ ID NO:4 proteins" or proteins "having a SEQ ID NO:4 sequence". As utilized herein "Belatacept" refers to SEQ ID NO:4 proteins.

CTLA4-Ig Monomers and Multimers

CTLA4-Ig molecules can include, for example, CTLA4-Ig proteins in monomer, dimer, trimer, tetramer, pentamer, hexamer, or other multimeric forms. CTLA4-Ig molecules can comprise a protein fusion with at least an extracellular domain of CTLA4 and an immunoglobulin constant region. CTLA4-Ig molecules can have wild-type or mutant sequences, for example, with respect to the CTLA4 extracellular domain and immunoglobulin constant region sequences. CTLA4-Ig monomers, alone, or in dimer, tetramer or other multimer form, can be glycosytated.

In some embodiments, the invention provides populations of CTLA4-Ig molecules that have at least a certain percentage of dimer or other multimer molecules. For example, the invention provides CTLA4-Ig molecule populations that are greater than 90%, 95%, 96%, 97%, 98%, 99%, or 99.5% CTLA4-Ig dimers. In one embodiment, the invention provides a CTLA4-Ig molecule population that comprises from about 95% to about 99.5% CTLA4-Ig dimer and from about 0.5% to about 5% of CTLA4-Ig tetramer. In another embodiment, the CTLA4-Ig molecule population comprises about 98% CTLA4-Ig dimer, about 1.5% CTLA4-Ig tetramer and about 0.5% CTLA4-Ig monomer.

In one embodiment, the invention provides a population of CTLA4-Ig molecules wherein the population is substantially free of CTLA4-Ig monomer molecules. Substantially free of CTLA4-Ig monomer molecules can refer to a population of CTLA4-Ig molecules that have less than 1%, 0.5%, or 0.1% of monomers.

In one embodiment, the invention provides a population of CTLA4-Ig molecules wherein the population is substantially free of CTLA4-Ig multimers that are larger than dimers, such as tetramers, hexamers, etc. Substantially free of CTLA4-Ig multimer molecules larger than dimers can refer to a population of CTLA4-Ig molecules that have less than 6%, 5%, 4%, 3%, 2%, 1%, 0.5%, or 0.1% of CTLA4-Ig multimers larger than dimeric form.

In one embodiment, a CTLA4-Ig monomer molecule can have, for example, the amino acid sequence of: (i) 26-383 of SEQ ID NO:2, (ii) 26-382 of SEQ ID NO:2 (iii) 27-383 of SEQ ID NO:2, or (iv) 27-382 of SEQ ID NO:2, or optionally (v) 25-382 of SEQ ID NO:2, or (vi) 25-383 of SEQ ID NO:2. When an expression cassette comprising the nucleic acid sequence of SEQ ID NO: 1 is expressed in CHO cells, the predominant monomer form expressed has the N-terminus amino acid residue of methionine (residue 27 of SEQ ID NO:2), which corresponds to the N-terminus amino acid residue of wild-type human CTLA4. However, because SEQ ID NO:1 also includes the coding sequence for an Oncostatin M Signal Sequence (nucleotides 11-88 of SEQ ID NO: 1), the expressed protein from SEQ ID NO:1 contains an Oncostatin M Signal Sequence. The signal sequence is cleaved from the expressed protein during the process of protein export from the cytoplasm, or secretion out of the cell. But cleavage can result in N-terminal variants, such as cleavage between amino acid residues 25 and 26 (resulting in an N-terminus of residue 26, i.e., the "Ala variant"), or between amino acid residues 24 and 25 (resulting in an N-terminus of residue 2, i.e., the "Met-Ala variant"), as opposed to cleavage between amino acid residues 26 and 27 (resulting in an N-terminus of residue 27). For example, the Met-Ala variant can be present in a mixture of CTLA4-Ig molecules at about 1%, and the Ala variant can be present in a mixture of CTLA4-Ig molecules at about 8-10%. In addition, the expressed protein from SEQ ID NO:1 can have C-terminus variants due to incomplete processing. The predominant C-terminus is the glycine at residue 382 of SEQ ID NO:2. In a mixture of CTLA4-Ig molecules, monomers having lysine at the C-terminus (residue 383 of SEQ ID NO:2) can be present, for example, at about 4-5%.

A CTLA4-Ig monomer molecule can comprise an extracellular domain of human CTLA4. In one embodiment, the extracellular domain can comprise the nucleotide sequence of nucleotides 89-463 of SEQ ID NO:1 that code for amino acids 27-151 of SEQ ID NO:2. In another embodiment, the extracellular domain can comprise mutant sequences of human CTLA4. In another embodiment, the extracellular domain can comprise nucleotide changes to nucleotides 89-463 of SEQ ID NO:1 such that conservative amino acid changes are made. In another embodiment, the extracellular domain can comprise a nucleotide sequence that is at least 75%, 80%, 85%, 90%, 95%, 96%, 97%, 98%, or 99% identical to nucleotides 89-463 of SEQ ID NO:1.

A CTLA4-Ig monomer molecule can comprise a constant region of a human immunoglobulin. This constant region can be a portion of a constant region; this constant region can have a wild-type or mutant sequence. The constant region can be from human IgG1, IgG2, IgG3, IgG4, IgM, IgA1, IgA2, IgD or IgE. The constant region can be from a light chain or a heavy chain of an immunoglobulin. Where the constant region is from an IgG, IgD, or IgA molecule, the constant region can comprise one or more of the following constant region domains: CL, CH1, hinge, CH2, or CH3. Where the constant region is from IgM or IgE, the constant region can comprise one or more of the following constant region domains: CL, CH1, CH2, CH3, or Cα4. In one embodiment, the constant region can comprise on or more constant region domains from IgG, IgD, IgA, IgM or IgE.

In one embodiment, a CTLA4-Ig monomer molecule comprises a modified human IgG1 hinge region (nucleotides 464-508 of SEQ ID NO: 1; amino acids 152-166 of SEQ ID NO:2) wherein the serines at amino acid residues 156, 162, and 165 of SEQ ID NO:2 have been engineered from cysteines present in the wild-type sequence.

In one embodiment, a CTLA4-Ig monomer molecule comprises a modified human IgG1 CH2 region and a wild-type CH3 region (the modified human IgG1 CH2 domain having nucleotides 509-838 of SEQ ID NO: 1 and amino acids 167-276 of SEQ ID NO:2; the human IgG1 CH3 domain having nucleotides 839-1159 of SEQ ID NO:1 and amino acids 277-383 of SEQ ID NO:2).

In one embodiment, a CTLA4-Ig molecule population comprises monomers having a sequence shown in any one or more of FIG. 7, 8, or 9 of the U.S. Pat. No. 7,094,874, issued on Aug. 22, 2006 and in U.S. patent applications published as Publication No. US20030083246 and US20040022787, which are hereby incorporated by reference in its entirety.

In one embodiment, a CTLA4-Ig tetramer molecule comprises two pairs or two dimers of CTLA4-Ig polypeptides, wherein each polypeptide has one of the following amino acid sequences: (i) 26-383 of SEQ ID NO:2, (ii) 26-382 of SEQ ID NO:2, (iii) 27-383 of SEQ ID NO:2, or (iv) 27-382 of SEQ ID NO:2, or optionally (v) 25-382 of SEQ ID NO:2, or (vi) 25-383 of SEQ ID NO:2. Each member of the pair of polypeptides or dimer is covalently linked to the other member, and the two pairs of polypeptides are non-covalently associated with one another thereby forming a tetramer. Such tetramer molecules are capable of binding to CD80 or CD86.

In another embodiment, such tetramer molecules can bind to CD80 or CD86 with an avidity that is at least 2-fold greater than the binding avidity of a CTLA4-Ig dimer (whose monomers have one of the above amino acid sequences) to CD80 or CD86. In another embodiment, such tetramer molecules can bind to CD80 or CD86 with an avidity that is at least 2-fold greater than the binding affinity or avidity of wild-type CTLA4 to CD80 or CD86. Such greater avidity can contribute to higher efficacy in treating immune disorders and other diseases as described below. In addition, greater or improved avidity can produce the result of higher potency of a drug. For example, a therapeutic composition comprising CTLA4-Ig tetramer would have a higher avidity and therefore higher potency than the same amount of a therapeutic composition having CTLA4-Ig monomer. In another embodiment, such tetramer molecules can have at least a 2-fold greater inhibition on T cell proliferation as compared to a CTLA4-Ig dimer (whose monomers have one of the above amino acid sequences). In another embodiment, such tetramer molecules can have at least a 2-fold greater inhibition on T cell proliferation as compared to a wild-type CTLA4 molecule.

T cell proliferation can be measured using standard assays known in the art. For example, one of the most common ways to assess T cell proliferation is to stimulate T cells via antigen or agonistic antibodies to TCR and to measure, for example, the incorporation of titrated thymidine (3H-TdR) in proliferating T cells or the amount of cytokines released by proliferating T cells into culture. The inhibitory effect of CTLA4-Ig molecules upon T cell activation or proliferation can thereby be measured.

The affinity of a CTLA4-Ig molecule is the strength of binding of the molecule to a single ligand, including CD80, CD86, or CD8OIg or CD86Ig fusion proteins. The affinity of CTLA4-Ig to ligands can be measured by using, for example, binding interaction analysis (BIA) based on surface plasmon technique. Aside from measuring binding strength, it permits real time determination of binding kinetics, such as association and dissociation rate constants. A sensor chip, consisting of a glass slide coated with a thin metal film, to which a surface matrix is covalently attached, is coated with one of the interactants, i.e, CTLA4-Ig or one of the ligands. A solution containing the other interactant is allowed to flow over its surface. A continuous light beam is directed against the other side of the surface, and its reflection angle is measured. On binding of CTLA4-Ig to the ligand, the resonance angle of the light beam changes (as it depends on the refractive index of the medium close to the reactive side of the sensor, which in turn is directly correlated to the concentration of dissolved material in the medium). It is subsequently analyzed with the aid of a computer.

In one embodiment, CTLA4-Ig binding experiments can be performed by surface plasmon resonance (SPR) on a BIAcore instrument (BIAcore AG, Uppsala, Sweden). CTLA4-Ig can be covalently coupled by primary amine groups to a carboxymethylated dextran matrix on a BIAcore sensor chip, thereby immobilizing CTLA4-Ig to the sensor chip. Alternatively, an anti-constant region antibody can be used to immobilize CTLA4-Ig indirectly to the sensor surface via the Ig fragment. Thereafter, ligands are added to the chip to measure CTLA4-Ig binding to the ligands. Affinity measurements can be performed, for example, as described in van der Merwe, P. et al., J. Exp. Med. (1997) 185 (3):393-404.

The avidity of CTLA4-Ig molecules can also be measured. Avidity can be defines as the sum total of the strength of binding of two molecules or cells to one another at multiple sites. Avidity is distinct from affininty which is the strength of binding one site on a molecule to its ligand. Without being bound by theory, higher avidity of CTLA4-Ig molecules can lead to increased potency of inhibition by CTLA4-Ig molecules on T-cell proliferation and activation. Avidity can be measured, for example, by two categories of solid phase assays: a) competitive inhibition assays, and b) elution assays. In both of them the ligand is attached to a solid support. In the competitive inhibition assay, CTLA4-Ig molecules are then added in solution at a fixed concentration, together with free ligand in different concentrations, and the amount of ligand which inhibits solid phase binding by 50% is determined. The less ligand needed, the stronger the avidity. In elution assays, the ligand is added in solution. After obtaining a state of equilibrium, a chaotrope or denaturant agent (e.g. isothiocyanate, urea, or diethylamine) is added in different concentrations to disrupt CTLA4-Ig/ligand interactions. The amount of CTLA4-Ig resisting elution is determined thereafter with an ELISA. The higher the avidity, the more chaotropic agent is needed to elute a certain amount of CTLA4-Ig. The relative avidity of a heterogeneous mixture of CTLA4-Ig molecules can be expressed as the avidity index (AI), equal to the concentration of eluting agent needed to elute 50% of the bound CTLA4-Ig molecules. Refined analysis of data can be performed by determining percentages of eluted CTLA4-Ig at different concentrations of the eluting agent.

Methods for Producing the CTLA4Ig Molecules of the Invention

Expression of CTLA4Ig molecules can be in prokaryotic cells. Prokaryotes most frequently are represented by various strains of bacteria. The bacteria may be a gram positive or a gram negative. Typically, gram-negative bacteria such as *E. coli* are preferred. Other microbial strains may also be used.

Sequences, described above, encoding CTLA4Ig molecules can be inserted into a vector designed for expressing foreign sequences in prokaryotic cells such as *E. coli*. These vectors can include commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al., (1977) Nature 198:1056), the tryptophan (trp) promoter system (Goeddel, et al., (1980) Nucleic Acids Res. 8:4057) and the lambda derived $P_L$ promoter and N-gene ribosome binding site (Shimatake, et al., (1981) Nature 292:128).

Such expression vectors will also include origins of replication and selectable markers, such as a beta-lactamase or neomycin phosphotransferase gene conferring resistance to antibiotics, so that the vectors can replicate in bacteria and cells carrying the plasmids can be selected for when grown in the presence of antibiotics, such as ampicillin or kanamycin.

The expression plasmid can be introduced into prokaryotic cells via a variety of standard methods, including but not limited to $CaCl_2$-shock (Cohen, (1972) Proc. Natl. Acad. Sci. USA 69:2110, and Sambrook et al. (eds.), "Molecular Cloning: A Laboratory Manual", 2nd Edition, Cold Spring Harbor Press, (1989)) and electroporation.

In accordance with the practice of the invention, eukaryotic cells are also suitable host cells. Examples of eukaryotic cells include any animal cell, whether primary or immortalized, yeast (e.g., *Saccharomyces cerevisiae, Schizosaccharomyces pombe*, and *Pichia pastoris*), and plant cells. Myeloma, COS and CHO cells are examples of animal cells that may be used as hosts. Particular CHO cells include, but are not limited to, DG44 (Chasin, et al., 1986 Som. Cell. Molec. Genet. 12:555-556; Kolkekar 1997 Biochemistry 36:10901-10909), CHO-K1 (ATCC No. CCL-61), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), and RR-CHOK1 designated ECACC 92052129 (CAMR, Salisbury, Wiltshire, UK). Illustrative plant cells include tobacco (whole plants, cell culture, or callus), corn, soybean, and rice cells. Corn, soybean, and rice seeds are also acceptable.

Nucleic acid sequences encoding CTLA4Ig molecules described above can also be inserted into a vector designed for expressing foreign sequences in a eukaryotic host. The regulatory elements of the vector can vary according to the particular eukaryotic host.

Commonly used eukaryotic control sequences for use in expression vectors include promoters and control sequences compatible with mammalian cells such as, for example, CMV promoter (CDM8 vector) and avian sarcoma virus (ASV) (πLN vector). Other commonly used promoters include the early and late promoters from Simian Virus 40 (SV40) (Fiers, et al., (1973) Nature 273:113), or other viral promoters such as those derived from polyoma, Adenovirus 2, and bovine papilloma virus. An inducible promoter, such as hMTII (Karin, et al., (1982) Nature 299:797-802) may also be used.

Vectors for expressing CTLA4Ig molecules in eukaryotes may also carry sequences called enhancer regions. These are important in optimizing gene expression and are found either upstream or downstream of the promoter region.

Examples of expression vectors for eukaryotic host cells include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSG5 vectors (Stratagene)), retroviral vectors (e.g., pFB vectors (Stratagene)), pcDNA-3 (Invitrogen) or modified forms thereof, adenoviral vectors; Adeno-associated virus vectors, baculovirus vectors, yeast vectors (e.g., pESC vectors (Stratagene)).

Nucleic acid sequences encoding CTLA4Ig molecules can integrate into the genome of the eukaryotic host cell and replicate as the host genome replicates. Alternatively, the vector carrying CTLA4Ig molecules can contain origins of replication allowing for extrachromosomal replication.

For expressing the nucleic acid sequences in *Saccharomyces cerevisiae*, the origin of replication from the endogenous yeast plasmid, the 2μ circle can be used. (Broach, (1983) Meth. Enz. 101:307). Alternatively, sequences from the yeast genome capable of promoting autonomous replication can be used (see, for example, Stinchcomb et al., (1979) Nature 282:39); Tschemper et al., (1980) Gene 10:157; and Clarke et al., (1983) Meth. Enz. 101:300).

Transcriptional control sequences for yeast vectors include promoters for the synthesis of glycolytic enzymes (Hess et al., (1968) J. Adv. Enzyme Reg. 7:149; Holland et al., (1978) Biochemistry 17:4900). Additional promoters known in the art include the CMV promoter provided in the CDM8 vector (Toyama and Okayama, (1990) FEBS 268:217-221); the promoter for 3-phosphoglycerate kinase (Hitzeman et al., (1980) J. Biol. Chem. 255:2073), and those for other glycolytic enzymes.

Other promoters are inducible because they can be regulated by environmental stimuli or the growth medium of the cells. These inducible promoters include those from the genes for heat shock proteins, alcohol dehydrogenase 2, isocytochrome C, acid phosphatase, enzymes associated with nitrogen catabolism, and enzymes responsible for maltose and galactose utilization.

Regulatory sequences may also be placed at the 3' end of the coding sequences. These sequences may act to stabilize messenger RNA. Such terminators are found in the 3' untranslated region following the coding sequences in several yeast-derived and mammalian genes.

Illustrative vectors for plants and plant cells include, but are not limited to, *Agrobacterium* T$_i$ plasmids, cauliflower mosaic virus (CaMV), and tomato golden mosaic virus (TGMV).

Mammalian cells can be transformed by methods including but not limited to, transfection in the presence of calcium phosphate, microinjection, electroporation, or via transduction with viral vectors.

Methods for introducing foreign DNA sequences into plant and yeast genomes include (1) mechanical methods, such as microinjection of DNA into single cells or protoplasts, vortexing cells with glass beads in the presence of DNA, or shooting DNA-coated tungsten or gold spheres into cells or protoplasts; (2) introducing DNA by making cell membranes permeable to macromolecules through polyethylene glycol treatment or subjection to high voltage electrical pulses (electroporation); or (3) the use of liposomes (containing cDNA) which fuse to cell membranes.

US patent application US Publication Number 20050019859 and US patent application US Publication Number 20050084933 teach processes for the production of proteins of the invention, specifically recombinant glycoprotein products, by animal or mammalian cell cultures and are herein incorporated by reference.

Following the protein production phase of the cell culture process, CTLA4Ig molecules are recovered from the cell culture medium using techniques understood by one skilled in the art. In particular, the CTLA4Ig molecule is recovered from the culture medium as a secreted polypeptide.

The culture medium is initially centrifuged to remove cellular debris and particulates. The desired protein subsequently is purified from contaminant DNA, soluble proteins, and polypeptides, with the following non-limiting purification procedures well-established in the art: SDS-PAGE; ammonium sulfate precipitation; ethanol precipitation; fractionation on immunoaffinity or ion-exchange columns; reverse phase HPLC; chromatography on silica or on an anion-exchange resin such as QAE or DEAE; chromatofocusing; gel filtration using, for example, Sephadex G-75 ™ column; and protein A Sepharose™ columns to remove contaminants such as IgG. Addition of a protease inhibitor, such as phenyl methyl sulfonyl fluoride (PMSF), or a protease inhibitor cocktail mix also can be useful to inhibit proteolytic degradation during purification. A person skilled in the art will recognize that purification methods suitable for a protein of interest, for example a glycoprotein, can require alterations to account for changes in the character of the protein upon expression in recombinant cell culture.

Purification techniques and methods that select for the carbohydrate groups of the glycoprotein are also of utility within the context of the present invention. For example, such techniques include, HPLC or ion-exchange chromatography using cation- or anion-exchange resins, wherein the more basic or more acidic fraction is collected, depending on which carbohydrate is being selected for. Use of such techniques also can result in the concomitant removal of contaminants.

The purification method can farther comprise additional steps that inactivate and/or remove viruses and/or retroviruses that might potentially be present in the cell culture medium of mammalian cell lines. A significant number of viral clearance steps are available, including but not limited to, treating with chaotropes such as urea or guanidine, detergents, additional ultrafiltration/diafiltration steps, conventional separation, such as ion-exchange or size exclusion chromatography, pH extremes, heat, proteases, organic solvents or any combination thereof.

The purified CTLA4Ig molecule require concentration and a buffer exchange prior to storage or further processing. A Pall Filtron TFF system may be used to concentrate and exchange the elution buffer from the previous purification column with the final buffer desired for the drug substance.

In one aspect, purified CTLA4Ig molecules, which have been concentrated and subjected to diafiltration step, can be filled into 2-L Biotainer® bottles, 50-L bioprocess bag or any other suitable vessel. CTLA4Ig molecules in such vessels can be stored for about 60 days at 2° to 8° C. prior to freezing. Extended storage of purified CTLA4Ig molecules at 2° to 8° C. may lead to an increase in the proportion of HMW species. Therefore, for long-term storage, CTLA4Ig molecules can be frozen at about −70° C. prior to storage and stored at a temperate of about −40° C. The freezing temperature can vary from about −50° C. to about −90° C. The freezing time can vary and largely depends on the volume of the vessel that contains CTLA4Ig molecules, and the number of vessels that are loaded in the freezer. For example, in one embodiment, CTLA4Ig molecules are in 2-L Biotainer® bottles. Loading of less than four 2-L Biotainer® bottles in the freezer may require from about 14 to at least 18 hours of freezing time. Loading of at least four bottles may require from about 18 to at least 24 hours of freezing time. Vessels with frozen CTLA4Ig molecules are stored at a temperature from about −35° C. to about −55° C. The storage time at a temperature of about −35° C. to about −55° C. can vary and can be as short as 18 hours. The frozen drug substance can be thawed in a control manner for formulation of drug product.

Co-pending U.S. patent application Ser. No. 60/752,267, filled on Dec. 20, 2005 and Ser. No. 06/849,543, filed on Oct. 5, 2006 and PCT patent application PCT/US06/49074 titled Cell Lines, Compositions and Methods for Producing a Composition with the inventor Kirk Leister filed on Dec. 19, 2006 teach processes for the production of proteins of the invention, specifically recombinant glycoprotein products, by animal or mammalian cell cultures and is herein incorporated by reference.

Lyophilized Formulation of the Invention

The lyophilized formulation of the invention comprises the CTLA4Ig molecule in a weight ratio of at least 1:2 protein to lyoprotectant. The lyoprotectant is preferably sugar, more preferably disaccharides, most preferably sucrose or maltose. The lyophilized formulation may also comprise one or more of the components selected from the list consisting of buffering agents, surfactants, bulking agents and preservatives.

During formulation development studies, the effects of various excipients on the solution- and freeze-dried solid-state stability of the CTLA4Ig molecule were evaluated.

Instability of the freeze-dried CTLA4Ig molecule in the absence of a stabilizer clearly highlighted a need for inclusion of a lyoprotectant in the formulation. Initial screening studies showed that drug product was stable in the presence of sugars such as maltose and sucrose and amino acids such as arginine and lysine. Polyols such as mannitol and polysaccharides such as dextran 40 were detrimental to its stability. The preferred lyoprotectants are the disaccharides maltose and sucrose.

Example VI describes stability studies of freeze dried Abatacept drug product in the presence of maltose stored at 50° C. An increase in high molecular weight (HMW) species was monitored using a stability-indicating size exclusion chromatography (SE-HPLC) assay. The results demonstrate that the stability of the CTLA4Ig molecule in a freeze-dried solid-state form is enhanced in the presence of maltose.

The amount of sucrose or maltose useful for stabilization of the lyophilized drug product is in a weight ratio of at least 1:2 protein to sucrose or maltose, preferably in a weight ratio of from 1:2 to 1:5 protein to sucrose or maltose, more preferably in a weight ratio of about 1:2 protein to maltose or sucrose.

If necessary, the pH of the formulation, prior to lyophilization, is set by addition of a pharmaceutically acceptable acid and/or base. The preferred pharmaceutically acceptable acid is hydrochloric acid. The preferred base is sodium hydroxide.

During formulation development, the stability of the freeze-dried drug product was studied as a function of pH. Example VI describes stability studies with freeze dried Abatacept drug product as a function of pH. The solution pH was adjusted between 6 to 8 prior to freeze-drying. The samples were placed on stability and the constituted product vials were monitored for an increase in the high molecular weight species at various time points using a stability-indicating size-exclusion chromatography (SE-HPLC) assay. Under the recommended storage condition of 2°-8° C., no significant changes in the rate of formation of HMW species were observed. Additionally; the solution-state stability data generated during an early development showed the pH of maximum stability to be between 7 and 8. The acceptable pH range for the lyophilized drug product is from 7 to 8 with a preferred target pH of 7.5.

In another aspect, the salts or buffer components may be added in an amount of at least about 10 mM, preferably 10-200 mM. The salts and/or buffers are pharmaceutically acceptable and are derived from various known acids (inorganic and organic) with "base forming" metals or amines. In addition to phosphate buffers, there can be used glycinate, carbonate, citrate buffers and the like, in which case, sodium, potassium or ammonium ions can serve as counterion.

A "bulking agent" is a compound which adds mass to a lyophilized mixture and contributes to the physical structure of the lyophilized cake (e.g. facilitates the production of an essentially uniform lyophilized cake which maintains an open pore structure). Illustrative bulking agents include mannitol, glycine, polyethylene glycol and sorbitol. The lyophilized formulations of the present invention may contain such bulking agents A preservative may be optionally added to the formulations herein to reduce bacterial action. The addition of a preservative may, for example, facilitate the production of a multi-use (multiple-dose) formulation.

One skilled in the art would select the amount of drug product to be filed into a vial depending on the required dosages and administration schedule for a specific treatment. For example, the concentration of CTLA4Ig per vial may range from 50 to 300 mg/vial, preferably 100 to 250 mg/vial.

A typical composition of lyophilized Abatacept drug product is listed in Table 1 below.

TABLE 1

Composition of lyophilized abatacept (250 mg/vial) drug product

| Component | Amount (mg/vial)[a] |
|---|---|
| Abatacept | 262.5 |
| Maltose monohydrate | 525 |
| Sodium phosphate monobasic, monohydrate[b] | 18.1 |
| Sodium chloride[b] | 15.3 |
| Hydrochloric Acid | Adjust to pH 7.5 |
| Sodium hydroxide | Adjust to pH 7.5 |

[a]includes a 5% overfill for vial, needle, syringe loss
[b]These components are present in the abatacept drug substance solution A typical composition of lyophilized Belatacept drug product is listed in Table 2 below.

TABLE 2

Composition of lyophilized Belatacept 100 mg/vial drug product

| Component | Amount/Vial (mg)[a] |
|---|---|
| Belatacept | 110[a] |
| Sucrose | 220 |
| Sodium Phosphate Monobasic Monohydrate | 15.18 |
| Sodium Chloride | 2.55 |
| 1N Sodium Hydroxide | Adjust to pH 7.5 |
| 1N Hydrochloric Acid | Adjust to pH 7.5 |

[a]Each vial contains 10% overfill for vial, needle and syringe holdup of the reconstituted solution.

The lyophilized drug product is constituted with an aqueous carrier. The aqueous carrier of interest herein is one which is pharmaceutically acceptable (safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g. phosphate-buffered saline), sterile saline solution, Ringer's solution or dextrose solution.

Preferably, the lyophilized drug product of the current invention is constituted with either Sterile Water for Injection, USP (SWFI) or 0.9% Sodium Chloride Injection, USP. During constitution, the lyophilized powder rapidly dissolves providing a clear, colorless solution.

Typically, the lyophilized drug product of the instant invention is constituted to about 25 mg/ml with 10 ml of either Sterile Water for injection, USP (SWFI) or 0.9% Sodium Chloride Injection, USP. The constituted solution is further diluted to drug product concentrations between 1 and 10 mg/ml with 0.9% Sodium Chloride Injection, USP. The diluted drug product for injection is isotonic and suitable for administration by intravenous infusion.

During early clinical development, the constituted solutions of lyophilized drug product were found to be incompatible with disposable siliconized syringes, which are commonly used for the preparation and administration of the parenteral products. Specifically, the constituted drug product solution developed thread-like, gelatinous particles when stored in these syringes for more than 10-15 minutes. Further studies demonstrated that this incompatibility was due to the interaction of drug product with silicone oil (dimethylsiloxane), which is used as a lubricant on these syringes. The formation of these particles did not affect the potency of the drug product solution over its use time. Silicone free syringes are preferably utilized for drug product constitution and transfer of the constituted solutions from the vial to the intravenous bag.

Alternatively, a surfactant may be added to the formulation to reduce or prevent the interaction of the constituted drug product with the siliconized syringe, for example, in an amount sufficient thereof.

The recommended storage condition for the lyophilized formulation is from 2-8° C. with a recommended shelf life of at least 12 months.

Preparation of the Lyophilized Formulation

The lyophilized drug product manufacturing process involves batching of the Formulated Bulk Solution for lyophilization, aseptic filtration, filling in vials, freezing vials in a freeze-dryer chamber, followed by lyophilization, stoppering and capping.

Examples III and IV describe the manufacture of the lyophilized. Abatacept and Belatacept drug products, respectively.

The Formulated Bulk Solution is typically set at a fixed protein concentration so that the desired vial fill volume can be kept constant. During the addition of lyoprotectant, the mixer speed is controlled at 250±50 rpm so as to minimize foaming in the batching solution and to ensure complete dissolution of the lyoprotectant within 10 to 20 minutes. The Formulated Bulk Solution can be stored under 2°-8° C. or room temperature and room light for at least 32 hours prior to lyophilization.

The Formulated Bulk Solution is not terminally sterilized due to heat sensitivity of the CTLA4Ig molecule. The Formulated Bulk Solution may be sterilized using two 0.22 µm Millipore Millipak® sterilizing grade filters in series prior to filling in vials for lyophilization.

The freeze-drying cycle selected for this product is optimized in order to have efficient sublimation and evaporation during the primary and secondary phases of drying respectively, without compromising the product quality.

To aid in rapid dissolution of the lyophilized powder and to prevent the formation of excessive foam during constitution of the drug product, the lyophilized vials are stoppered under 500±100 microns chamber pressure at the end of the freeze-drying cycle.

One skilled in the art would be aware of the need to overfill the container so as to compensate for vial, needle, syringe hold-up during preparation and injection. For example, each vial of Abatacept drug product, 250 mg/ml, contains a 5% overage of drug product to account for reconstitution and withdrawal losses.

Liquid Subcutaneous Formulation

One skilled in the art would recognize the inconvenience of an IV formulation for the patient in need of frequent, chronic therapy. The patient has to make frequent trips to the hospital to receive their drug via an IV infusion that may last as long as an hour. Consequently, a SC formulation that could be self-administered at home would be very beneficial to such a patient.

For subcutaneous administration, a dosage form with high protein concentrations is desired. Treatments with high doses of more than 1 mg/kg (>100 mg per dose) require development of formulations at concentrations exceeding 100 mg/ml because of the small volume (<1.5 ml) that can be given by the SC routes. In order to optimize the long term stability at high concentration against formation of high molecular weight species, formulation development studies were conducted to evaluate the effect of various excipients on the solution state stability of the liquid SC formulations of the invention.

The SC formulation of the invention comprises the CTLA4Ig molecule at a protein concentration of at least 100 mg/ml in combination with a sugar at stabilizing levels, preferably a protein concentration of at least 125 mg/ml in combination with a sugar at stabilizing levels, in an aqueous carrier. The sugar is preferably in a weight ratio of at least 1:1.1 protein to sugar. The stabilizer is preferably employed in an amount no greater than that which may result in a viscosity undesirable or unsuitable for administration via SC syringe. The sugar is preferably disaccharides, most preferably sucrose. The SC formulation may also comprise one or more of the components selected from the list consisting of buffering agents, surfactants, and preservatives.

The stability profile of the SC formulation was evaluated in presence of various stabilizers including sugars, polysaccharides, amino acids, surfactants, polymers, cyclodextrans, proteins, etc. Among all the excipients evaluated, sugars such as sucrose, mannitol and trehalose had a better stabilizing effect against the formation of high molecular weight species.

Examples V and VIII describe stability studies of SC Belatacept and Abatacept drug product, respectively, in the presence of sucrose stored at various temperatures for various time periods. An increase in high molecular weight species was monitored using a stability-indicating size exclusion chromatography (SE-HPLC) assay. The results demonstrate that the stability of the CTLA4Ig molecule in the SC formulation is enhanced in the presence of sucrose. Stabilization by sucrose was better at higher sucrose:protein weight ratio. Based on these studies, sucrose was selected as the stabilizer at a ratio that provides optimum stability without resulting in a SC solution with excessive hypertonicity.

The amount of sucrose useful for stabilization of the SC drug product is in a weight ratio of at least 1:1 protein to sucrose, preferably in a weight ratio of from 1:1.3 to 1:5 protein to sucrose, more preferably in a weight ratio of about 1:1.4 protein to sucrose.

If necessary, the pH of the formulation is set by addition of a pharmaceutically acceptable acid and/or base. The preferred pharmaceutically acceptable acid is hydrochloric acid. The preferred base is sodium hydroxide.

During formulation development, the stability of the SC drug product was studied as a function of pH. Example V describes stability studies with SC Belatacept drug product as a function of pH. The SC formulation pH was adjusted between 7 to 8.2, samples were placed on stability and the drug product was monitored for an increase in the high molecular weight species at various time points using a stability-indicating size-exclusion chromatography (SE-HPLC) assay. Under the recommended storage condition of 2°-8° C., no significant changes in the rate of formation of HMW species were observed after 3 months.

In addition to aggregation, deamidation is a common product variant of peptides and proteins that may occur during fermentation, harvest/cell clarification, purification, drug substance/drug product storage and during sample analysis. Deamidation is the loss of $NH_3$ from a protein forming a succinimide intermediate that can undergo hydrolysis. The succinimide intermediate results in a 17 u mass decrease of the parent peptide. The subsequent hydrolysis results in an 18 u mass increase. Isolation of the succinimide intermediate is difficult due to instability under aqueous conditions. As such, deamidation is typically detectable as 1 u mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation.

Preliminary laboratory scale stability studies suggest that deamidation will exceed reference levels of the peptide mapping test method at 24 months using the SC abatacept formulation at pH 7.8. The data at six months under both 2-8° C. and 25° C. at 60% humidity showed that the rate of demaidation was lower at pH 7.2 and higher at pH 8 when compared to the SC abatacept sample at pH 7.8. Examples IX and XII describe laboratory scale pH studies designed to evaluate deamidation in SC drug product formulations in the pH range of 6.3 to 7.2.

The acceptable pH range for the SC drug product is from 6 to 8, preferably 6 to 7.8, more preferably 6 to 7.2.

In another aspect, the salts or buffer components may be added in an amount of at least 10 mM, preferably 10-200 mM. The salts and/or buffers are pharmaceutically acceptable and are derived from various known acids (inorganic and organic) with "base forming" metals or amines. In addition to phosphate buffers, there can be used glycinate, carbonate, citrate buffers and the like, in which case, sodium, potassium or ammonium ions can serve as counterion.

Example VIII describes the effect of buffer strength on Abatacept SC drug product. Stability was better in 10 mM phosphate buffer compared to 5 mM phosphate buffer at pH 7.5 at 100 mg/mL abatacept drug product concentration. Moreover the higher buffering capacity of 10 mM phosphate buffer offered better pH control of the formulation compared to 5 mM buffer.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g. phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

As discussed with the lyophilized drug product, the CTLA4Ig molecule is incompatible with silicone found in standard syringes, in that, it interacts with silicone to form visible particulates, thereby limiting the patient to utilizing silicone free syringes. The SC formulation may optionally comprise a surfactant to prevent formation of visible particulates in presence of silicone Examples V and VIII describe the effect of surfactants such as Polysorbate 80 and Poloxamer 188 on the solution stability of belatacept and abatacept drug product, respectively, and it was found that surfactants did not, have an effect on the stability of the CTLA4Ig molecule in a SC formulation. Different levels of Poloxamer 188 were evaluated and the concentration of from 4 mg/ml to 8 mg/ml, preferable 8 mg/ml was found to be adequate to prevent the silicone related particulate formation in the formulation.

A typical composition of belatacept SC drug product, 125 mg/ml (100 mg/vial) drug product is provided in Table 3 below.

TABLE 3

Composition of Belatacept SC drug product, 125 mg/ml (100 mg/vial)

| Component | Amount (mg/vial)[b] |
|---|---|
| Belatacept | 140.0 |
| Sucrose | 190.4 |
| Poloxamer 188 | 8.96 |
| Sodium phosphate monobasic, monohydrate | 0.371 |
| Sodium phosphate dibasic, anhydrous | 1.193 |
| Water for Injection | q.s. to 1.12 ml |

[b]Includes 40% overfill for Vial, Needle, Syringe loss

A typical composition of abatacept SC drug product, 125 mg/ml (125 mg/vial) is provided in Table 4 below.

TABLE 4

Composition of Abatacept SC drug product, 125 mg/ml (125 mg/vial)

| Component | Amount (mg/vial)[c] |
|---|---|
| Abatacept | 175 |
| Sucrose | 238 |
| Poloxamer 188 | 11.2 |
| Sodium phosphate monobasic, monohydrate | 0.20 |
| Sodium phosphate dibasic, anhydrous | 136 |
| Water for Injection | q.s. to 1.4 ml |

[c] Includes 40% overfill for Vial, Needle, Syringe loss

A typical composition of abatacept SC drug product, 125 mg/ml filed into a syringe is provided in Table 5 below.

TABLE 5

Composition of Abatacept SC drug product, 125 mg/ml (125 mg/syringe)

| Component | Amount (mg/syringe) |
|---|---|
| Abatacept | 125 |
| Sucrose | 170 |
| Poloxamer 188 | 8.0 |
| Sodium phosphate monobasic, monohydrate | 0.143 |
| Sodium phosphate dibasic, anhydrous | 0.971 |
| Water for Injection | q.s. to 1 ml |

The recommended storage condition for the SC formulation is from 2-8° C. with a recommended shelf life of at least 12 months.

The density of the abatacept SC drug product and the matching placebo was determined at ambient temperature using the Mettler-Toledo densitometer. Measurements were performed using 5-mL samples in triplicates. The density of the abatacept SC formulation was found to be 1.1 g/cc and that of the placebo product was found to be 1.065 g/cc. Typically, the density of a SC CTLA4Ig formulation is about 1.0 g/cc to about 1.2 g/cc, preferably about 1.0 g/cc to about 1.15 Wee, more preferably about 1.095 glee to about 1.105 glee.

The viscosity of the abatacept SC formulation was determined using the Brookfield rheometer at ambient temperature. A reference standard of 9.3 cps was used for the measurements. The viscosity of the SC drug product at 125 mg/mL abatacept concentration was found to be 13±2 cps. Typically, the viscosity of a SC CTLA4Ig formulation at 125 mg/mL is about 9 to about 20 cps, preferably about 9 to about 15 cps, more preferably 12 to about 15 cps.

Osmolality of SC abatacept drug product and placebo formulation was measured using a vapor pressure method. The data show that at concentrations of 125 mg/mL, the osmolality of abatacept SC formulation is 770±25 mOsm/kgH$_2$O Typically, the osmolatlity of a SC CTLA4Ig formulation at 125 mg/mL is about 250 to about 800 mOsm/kgH$_2$O, preferably about 700 to about 800 mOsm/kgH$_2$O, more preferably about 750 to about 800 mOsm/kgH$_2$O.

Preparation of the SC Formulation

The manufacturing process developed for SC formulations typically involves compounding with sugar and surfactant, followed by aseptic sterile filtration and filling into vials or syringes, optionally preceded by diafiltration (buffer exchange) and concentration of drug substance using an ultrafiltration unit.

Examples I and II describe the manufacture of the SC Belatacept and Abatacept, drug products, respectively.

One skilled in the art would be aware of the need to overfill the container so as to compensate for vial, needle, syringe hold-up during preparation and injection. For example, a 40% overage of drug product is incorporated into each vial of SC liquid formulation to account for withdrawal losses and guarantee that 0.8 ml of the solution containing 100 mg of belatacept drug product can be withdrawn from the vial.

Liquid Formulation

IV formulations may be the preferred administration route in particular instances, such as when a patient is in the hospital after transplantation receiving all drugs via the IV route. One skilled in the art would recognize the disadvantages and risks of a lyophilized formulation for both the manufacturer and the health care professional, respectively. The risks and disadvantages to the health care professional associated with reconstitution can include contamination, foaming and product loss as well the health care professional's time required to prepare the IV formulation. Additionally, the manufacturer's costs in equipment and employee time can be decreased by removing the lyophilization step of a manufacturing process. All of these reasons are sufficient motivation to design a liquid formulation for IV use.

The preferred liquid formulation to develop would be a formulation that would mimic the lyophilized drug product after the first constitution to a protein concentration of about 25 mg/ml. The purchased liquid formulation would then be further diluted to the desired drug product concentrations between 1 and 10 mg/ml with 0.9% Sodium Chloride Injection, USP by the health care professional at time of use. The diluted drug product for injection is isotonic and suitable for administration by intravenous infusion.

As discussed above, long term stability of liquid formulations is an issue for protein drug products. In order to confirm the long term stability of a solution against formation of high molecular weight species, formulation development studies were conducted to evaluate the solution state stability of the liquid formulation of the invention.

The liquid formulation of the invention comprises the CTLA4Ig molecule at a protein concentration of at least 20 mg/ml in combination with a sugar at stabilizing levels, preferably at least 25 mg/ml in combination with a sugar at stabilizing level in an aqueous carrier. Preferably the sugar is in a weight ratio of at least 1:1 protein to sugar. The sugar is preferably disaccharides, most preferably sucrose. The liquid formulation may also comprise one or more of the components selected from the list consisting of buffering agents, surfactants, and preservatives.

The amount of sucrose useful for stabilization of the liquid drug product is in a weight ratio of at least 1:1 protein to sucrose, preferably in a weight ratio of from 1:2 to 1:10 protein to sucrose, more preferably in a weight ratio of about 1:2 protein to sucrose.

If necessary, the pH of the formulation is set by addition of a pharmaceutically acceptable acid and/or base. The preferred pharmaceutically acceptable acid is hydrochloric acid. The preferred base is sodium hydroxide.

During formulation development, the stability of the liquid drug product was studied at a target pH of 7.5. Example VII describes stability studies with liquid Belatacept drug product, at a pH of 7.5. The liquid formulation pH was adjusted to 7.5, samples were placed on stability and the drug product was monitored for an increase in the high molecular weight species at various time points using a stability-indicating size-exclusion chromatography (SE-HPLC) assay. Under the recommended storage condition of 2°-8° C., no significant changes in the rate of formation of HMW species were observed.

In addition to aggregation, deamidation and fragmentation are product variant of peptides and proteins that may occur during fermentation, harvest/cell clarification, purification, drug substance/drug product storage and during sample analysis. Preliminary laboratory scale stability studies suggest that deamidation will exceed reference levels of the peptide mapping test method (rise above the 5% T26a or T26b (% T30) maximum) and that fragmentation will exceed reference levels for the SDS-PAGE test method (drop below the 96% major band minimum) at 24 months using the belatacept (20 mg/ml at pH 7.5) stored at 2°-8° C. Data from liquid formulations (see SC data above) show that the rate of deamidation found in the formulations of the invention decreases as the pH of the formulations is lowered.

The acceptable pH range for the liquid drug product is from 6 to 8 preferably 6 to 7.8, more preferably 6 to 7.2.

In another aspect, the salts or buffer components may be added in an amount of at least about 10 mM, preferably 10-200 mM. The salts and/or buffers are pharmaceutically acceptable and are derived from various known acids (inorganic and organic) with "base forming" metals or amines. In addition to phosphate buffers, there can be used glycinate, carbonate, citrate buffers and the like, in which case, sodium, potassium or ammonium ions can serve as counterion.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g. phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

As discussed with the lyophilized drug product, the CTLA4Ig molecule is incompatible with silicone found in standard syringes, in that, it interacts with silicone to form visible particulates, thereby limiting the health care professional to utilizing silicone free syringes. The liquid formulation may optionally comprise a surfactant to prevent formation of visible particulates in presence of silicone.

A typical composition of Belatacept liquid drug product, 20 mg/ml (250 mg/vial) drug product is provided in Table 6 below.

TABLE 6

Composition of Belatacept liquid drug product, 20 mg/ml (250 mg/vial)

| Component | Amount[a] (mg/vial) |
| --- | --- |
| Belatacept | 260 |
| Sucrose | 520 |
| Sodium phosphate monobasic, monohydrate | 18.1 |
| Sodium chloride | 15.3 |
| Hydrochloric acid | Adjust to pH 7.5 |
| Sodium hydroxide | Adjust to pH 7.5 |
| Water for Injection | q.s. to 13 ml |

[a]includes 4% overfill for vial, needle and syringe losses

The recommended storage condition for the liquid formulation is from 2-8° C. with a recommended shelf life at least 12 months.

Preparation of the Liquid Formulation

The liquid drug product manufacturing process typically involves compounding with sugar and optionally surfactant followed by aseptic filtration and filling in vials, stoppering and capping.

The Formulated Bulk Solution is typically set at a fixed protein concentration so that the desired vial fill volume can be kept constant. During the addition of sugar to drug substance, the mixer speed is controlled at 250±50 rpm so as to minimize foaming in the batching solution and to ensure complete dissolution of the sugar within 10 to 20 minutes. The Formulated Bulk Solution can be stored under 2°-8° C. or room temperature and room light for at least 24 hours prior to filling.

The Bulk Solution is not terminally sterilized due to heat sensitivity of the CTLA4Ig molecule. The Bulk Solution may be sterilized using two 0.22-µm Millipore Millipak® sterilizing grade filters in series prior to filling in vials.

One skilled in the art would be aware of the need to overfill the container so as to compensate for vial, needle, syringe hold-up during preparation and injection. For example, each vial of Belatacept drug product, 20 mg/mL (250 mg/vial), contains a 4% overage of drug product to account for reconstitution and withdrawal losses.

Articles of Manufacture

In another embodiment of the invention, an article of manufacture is provided which contains the drug product and preferably provides instructions for its use. The article of manufacture comprises a container. Suitable containers include, for example, bottles, vials, syringes and test tubes. The container may be formed from a variety of materials such as glass, plastic or metals.

The container holds the lyophilized or liquid formulations. The label on, or associated with, the container may indicate directions for reconstitution and/or use. For example, the label may indicate that the 25 mg/ml belatacept drug product is to be diluted to protein concentrations as described above. The label may further indicate that the SC formulation is useful or intended for subcutaneous administration. The container holding the formulation may be a multi-use vial, which allows for repeat administrations (e.g. from 2-6 administrations) of, for example, the subcutaneous formulation. Alternatively, the container may be a pre-filled syringe containing, for example, the subcutaneous formulation.

The article of manufacture may further comprise a second container comprising, for example, a suitable carrier for the lyophilized formulation.

The article of manufacture may further include other materials desirable from a commercial and user standpoint, including other buffers, diluents, filters, needles, syringes, and package inserts with instructions for use.

Silicone free syringes are preferably utilized for surfactant free drug product, such as upon reconstitution of lyophilized drug product and/or transfer of the solutions from the vial to the intravenous bag and may be co-packaged with the drug product vial.

Methods of Use

The present invention further provides methods for treating immune system diseases or tolerance induction comprising administering an effective amount of the CTLA4Ig molecule formulations of the invention. In particular embodiments, the immune system diseases are mediated by CD28- and/or CTLA4-positive cell interactions with CD80/CD86-positive cells. In a further embodiment, T cell interactions are inhibited. Immune system diseases include, but are not limited to, autoimmune diseases, immunoproliferative diseases, and graft-related disorders. These methods comprise administering to a subject the CTLA4Ig molecule formulations of the invention to regulate T cell interactions with the CD80- and/or CD86-positive cells. Examples of graft-related diseases include graft versus host disease (GVHD) (e.g., such as may result from bone marrow transplantation, or in the induction of tolerance), immune disorders associated with graft transplantation rejection, chronic rejection, and tissue or cell allo- or xenografts, including solid organs, skin, islets, muscles, hepatocytes, neurons. Examples of immunoproliferative diseases include, but are not limited to, psoriasis; T cell lymphoma; T cell acute lymphoblastic leukemia; testicular angiocentric T cell lymphoma; benign lymphocytic angiitis; and autoimmune diseases such as lupus (e.g., lupus erythematosus, lupus nephritis), Hashimoto's thyroiditis, primary myxedema, Graves' disease, pernicious anemia, autoimmune atrophic gastritis, Addison's disease, diabetes (e.g. insulin dependent diabetes mellitus, type I diabetes mellitis), good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjogren's syndrome, rheumatic diseases (e.g., rheumatoid arthritis), polymyositis, scleroderma, and mixed connective tissue disease.

The present invention further provides a method for inhibiting solid organ and/or tissue transplant rejections by a subject, the subject being a recepient of transplant tissue. Typically, in tissue transplants, rejection of the graft is initiated through its recognition as foreign by T cells, followed by an immune response that destroys the graft. The CTLA4Ig molecule formulations of this invention, by inhibiting T lymphocyte proliferation and/or cytokine secretion, may result in reduced tissue destruction and induction of antigen-specific T cell unresponsiveness may result in long-term graft acceptance without the need for generalized immunosuppression. Furthermore, the CTLA4Ig molecule formulations of the invention can be administered with other pharmaceuticals including, but not limited to, corticosteroids, cyclosporine, rapamycin, mycophenolate mofetil, azathioprine, tacrolismus, basiliximab, and/or other biologics.

The present invention also provides methods for inhibiting graft versus host disease in a subject. This method comprises administering to the subject the formulations of the invention, alone or together, with further additional ligands, reactive with IL-2, IL-4, or γ-interferon. For example, a CTLA4Ig molecule SC formulation of this invention may be administered to a bone marrow transplant recipient to inhibit the alloreactivity of donor T cells. Alternatively, donor T cells within a bone marrow graft may be tolerized to a recipient's alloantigens ex vivo prior to transplantation.

Inhibition of T cell responses by CTLA4Ig molecule formulations of the invention may also be useful for treating autoimmune disorders. Many autoimmune disorders result from inappropriate activation of T cells that are reactive against autoantigens, and which promote the production of cytokines and autoantibodies that are involved in the pathology of the disease. Administration of a CTLA4Ig molecule formulation in a subject suffering from or susceptible to an autoimmune disorder may prevent the activation of autoreactive T cells and may reduce or eliminate disease symptoms. This method may also comprise administering to the subject a formulation of the invention, alone or together, with further additional ligands, reactive with IL-2, IL-4, or γ-interferon.

The most effective mode of administration and dosage regimen for the formulations of this invention depends upon the severity and course of the disease, the patient's health and response to treatment and the judgment of the treating physician. In accordance with the practice of the invention an effective amount for treating a subject may be between about 0.1 and about 10 mg/kg body weight of subject. Also, the effective amount may be an amount between about 1 and about 10 mg/kg body weight of subject.

The CTLA4Ig molecule formulations of the invention may be administered to a subject in an amount and for a time (e.g. length of time and/or multiple times) sufficient to block endogenous B7 (e.g., CD80 and/or CD86) molecules from binding their respective ligands, in the subject. Blockage of endogenous B7/ligand binding thereby inhibits interactions between B7-positive cells (e.g., CD80- and/or CD86-positive cells) with CD28- and/or CTLA4-positive cells. Dosage of the CTLA4Ig molecule is dependant upon many factors including, but not limited to, the type of tissue affected, the type of disease being treated, the severity of the disease, a subject's health, and a subject's response to the treatment with the agents. Accordingly, dosages of the agents can vary depending on the subject and the mode of administration, US patent application US Publication Number US 2003/0083246 and US patent application US Publication Number US 2004/0022787 teach dosage and administration schedules for CTLA4Ig having the amino acid sequence shown in SEQ ID NO:2 for treating rheumatic diseases, such as rheumatoid arthritis. All are herein incorporated by reference An effective amount of CTLA4Ig molecule may be administered to a subject daily, weekly, monthly and/or yearly, in single or multiple times per hour/day/week/month/year, depending on need. For example, in one embodiment, an effective amount of the CTLA4Ig molecule may initially be administered once every two weeks for a month, and then once every month thereafter.

An effective amount of CTLA4Ig molecule is an amount about 0.1 to 100 mg/kg weight of a subject. In another embodiment, the effective amount is an amount about 0.1 to 20 mg/kg weight of a subject. In a specific embodiment, the effective amount of CTLA4Ig is about 2 mg/kg weight of a subject. In another specific embodiment, the effective amount of CTLA4Ig is about 10 mg/kg weight of a subject. In another specific embodiment, an effective amount of CTLA4Ig is 500 mg for a subject weighing less than 60 kg, 750 mg for a subject weighing between 60-100 kg and 1000 mg for a subject weighing more than 100 kg.

U.S. patent application Ser. No. 60/668,774, filed Apr. 6, 2005 and U.S. patent application Ser. No. 11/399,666, filed Apr. 6, 2006 teach the dosage and administration schedule for LEA29YIg having the amino acid sequence shown in SEQ ID NO:4 for treating immune disorders associated with graft transplantation. All are herein incorporated by reference.

Typically, doses of the CTLA4Ig molecule formulation of the invention are based on body weight, and administration regimens may be dictated by the target serum trough profiles. Typically, target trough serum concentration of LEA29YIg molecules of the invention between about 3 µg/mL and about 30 µg/mL over the first 3 to 6 months post-transplant will be sufficient to maintain function of the allograft, preferably between about 5 µg/mL and about 20 µg/mL. Typically, target trough serum concentration of LEA29YIg molecules of the invention during the maintenance phase are between about 0.2 µg/mL and about 3 µg/mL, preferably between about 0.25 µg/mL and about 2.5 µg/mL.

The LEA29YIg molecules of the invention may be administered in an amount between about 0.1 to about 20.0 mg/kg weight of the patient, typically between about 1.0 to about 15.0 mg/kg. For example, L104EA29YIg may be administered at 10 mg/kg weight of the patient during the early phase, high risk period that follows transplantation and decreased to 5 mg/kg weight of the patient for a maintenance dosage.

The administration of the CTLA4Ig molecules of the invention can be via a 30 minute to one or more hour intravenous infusion. Alternatively, single to multiple subcutaneous injections can deliver the required dosage. Typically, a 30 minute intravenous infusion is the administration route utilized during the early phase of treatment while the patient is in the hospital and/or making scheduled visits to the healthcare professional for monitoring. The subcutaneous injection is the typical administration mode utilized during the maintenance phase, thereby allowing the patient to return to their normal schedule by decreasing the visits to a healthcare professional for intravenous infusions.

Example 10 describes the pharmacokinetics of the lyophilized IV CTLA4Ig formulation in healthy subjects and patients with rheumatoid arthritis (RA). The pharmacokinetics of abatacept in RA patients and healthy subjects appeared to be comparable. In RA patients, after multiple intravenous infusions, the pharmacokinetics of abatacept showed proportional increases of $C_{max}$ and AUC over the dose range of 2 mg/kg to 10 mg/kg. At 10 mg/kg, serum concentration appeared to reach a steady-state by day 60 with a mean (range) trough concentration of 24 mcg/mL (from about 1 to about 66 mcg/mL). No systemic accumulation of abatacept occurred upon continued repeated treatment with 10 mg/kg at monthly intervals in RA patients.

The invention will be more fully understood by reference to the following examples. They should not, however, be construed as limiting the scope of the invention. All citations throughout the disclosure are hereby expressly incorporated by reference.

EXAMPLE I

Belatacept SC, 125 mg/ml (100 mg/vial) drug product is formulated as a sterile, non-pyrogenic ready-to-use solution suitable for subcutaneous administration.

Belatacept SC drug product, 125 mg/ml (100 mg/vial) is manufactured at 2.2 kg scale (1500 vials). The batch formula is provided in Table 7 below.

TABLE 7

Representative Batch Formula

| Component | Amount Per Batch (g) |
| --- | --- |
| Belatacept drug substance[b] | 250.0 |
| Sucrose | 340.0 |
| Poloxamer 188 | 16.0 |
| Sodium phosphate monobasic, monohydrate | 0.662 |
| Sodium phosphate dibasic, anhydrous | 2.13 |
| Water for Injection | q.s. to 2.2 kg |
| Total Batch Size (kg) | 2.2 kg[a] |

[a]Total batch size 2.2 kg (2-L). The density of the solution is 1.10 g/ml (at 20°-25° C.)
[b]Belatacept drug substance: protein concentration 25 mg/ml, 25 mM sodium phosphate, 10 mM sodium chloride, pH of 7.5, <5% HMW species The manufacturing process for Belatacept SC drug product, 125 mg/ml (100 mg/vial) drug product involves buffer exchange of the bulk drug substance from 25 mM sodium phosphate, 10 mM sodium chloride buffer at a pH of 7.5 to 10 mM sodium phosphate pH 7.5 buffer, followed by concentration of the protein from ~25 mg/ml to ~150 mg/ml by removal of buffer. The buffer exchange is accomplished by five times diafiltration of the bulk drug substance against the new 10 mM sodium phosphate pH 7.5 buffer, followed by concentration of protein to ~150 mg/ml by removal of buffer. A stainless steel Pelicon mini filter holder (Millipore) is equipped with stainless steel pressure gauges and membrane valves on the feed, retentate and permeates port. Two filtration cassettes used with Pellicon mini module are fitted with 0.1 m² area Biomax polyethersulfone membrane with 30 kDa nominal molecular weight cutoff limit. The filtration cassettes are installed according to the manufacturer's recommendations. The feed container for the drug substance is a 4 liter glass container with magnetic stir bar. MasterFlex high performance silicone tubing is used to connect the feed container to the filter holder and for the permeate line. Feed flow is provided by peristaltic pump installed in the feed line. Sucrose and Poloxamer 188 are then dissolved in the concentrated protein solution and final batch weight is adjusted with 10 mM sodium phosphate buffer, pH 7.5. The bulk solution is filtered through 0.22 micron sterilizing filter and filled into sterilized and depyrogenated 5-cc Type I flint glass vials, stoppered with 20 mm rubber stoppers and sealed with 20 mm aluminum flip-off seals. The composition of Belatacept SC drug product, 125 mg/ml (100 mg/vial) drug product is provided in Table 8 below.

TABLE 8

Composition of Belatacept SC drug product, 125 mg/ml (100 mg/vial)

| Component | Amount (mg/vial)[d] |
| --- | --- |
| Belatacept | 140.0 |
| Sucrose | 190.4 |
| Poloxamer 188 | 8.96 |
| Sodium phosphate monobasic, monohydrate | 0.371 |
| Sodium phosphate dibasic, anhydrous | 1.193 |
| Water for Injection | q.s. to 1.12 ml |

[d]Includes 40% overfill for Vial, Needle, Syringe loss

EXAMPLE II

Abatacept SC, 125 mg/ml (125 mg/vial) drug product is formulated as a sterile, non-pyrogenic ready-to-use solution suitable for subcutaneous administration. A batch of Abatacept SC, 125 mg/ml (125 mg/vial) drug product is manufactured at 5-L scale (3,500 vials). The batch formula is described in Table 9 below.

TABLE 9

Batch Formula

| Component | Amount (gm) |
| --- | --- |
| Abatacept drug substance[a] | 625 |
| Sucrose | 850 |
| Poloxamer 188 | 40 |
| Sodium phosphate monobasic, monohydrate | 0.715 |
| Sodium phosphate dibasic, anhydrous | 4.86 |
| Water for Injection | q.s. to 5.0 L |
| Total Batch size (L) | 5.0 |

[a]Abatacept drug substance: protein concentration 50 mg/ml, 25 mM sodium phosphate, 50 mM sodium chloride, pH of 7.5, <5% HMW species As described above in Example I, the manufacturing process for Abatacept SC, 125 mg/ml (125 mg/vial) drug product involves buffer exchange of the bulk drug substance from 25 mM sodium phosphate, 50 mM sodium chloride at a pH of 7.5 to 10 mM sodium phosphate pH 7.8 buffer, followed by concentration of the protein from ~50 mg/ml to ~150 mg/ml by removal of buffer. Sucrose and Poloxamer 188 are then dissolved in the concentrated protein solution and final batch weight is adjusted with 10 mM sodium phosphate buffer, pH 7.8. The bulk solution is filtered through 0.22 micron sterilizing filter and filled into sterilized and depyrogenated 5-cc Type I flint glass vials, stoppered with 20 mm rubber stoppers and sealed with 20 mm aluminum flip-off seals.

The composition of Abatacept SC drug product, 125 mg/ml (125 mg/vial) is provided in Table 10 below.

TABLE 10

Composition of Abatacept SC, 125 mg/ml (125 mg/vial) drug product

| Component | Amount (mg/vial)[e] |
| --- | --- |
| Abatacept | 175 |
| Sucrose | 238 |
| Poloxamer 188 | 11.2 |
| Sodium phosphate monobasic, monohydrate | 0.20 |
| Sodium phosphate dibasic, anhydrous | 1.36 |
| Water for Injection | q.s. to 1.4 ml |

[e] Includes 40% overfill for Vial, Needle, Syringe loss

EXAMPLE III

Abatacept, lyophilized, (250 mg/vial) drug product is a sterile, non-pyrogenic lyophile suitable for intravenous (IV) administration. Each single-use vial contains 250 mg of abatacept which is constituted with Sterile Water for Injection, USP and further diluted with 0.9% Sodium Chloride Injection, USP, at the time of use.

The batch formula for a 115 liter batch size is described in Table 11 below.

TABLE 11

Batch formula

| Component | Amount (kg) |
| --- | --- |
| Abatacept drug substance[a] | 4.6 |
| Maltose monohydrate | 9.2 |
| Hydrochloric Acid | Adjust to pH 7.5 |
| Sodium hydroxide | Adjust to pH 7.5 |
| Water for Injection | q.s. to 119.6[b] |

[a]abatacept drug substance: protein concentration 50 mg/ml, 25 mM sodium phosphate, 50 mM sodium chloride, pH of 7.5, <5% HMW species
[b]formulated bulk solution density = approx. 1.04 g/ml The required quantity of abatacept drug substance is added to a cleaned and sterilized stainless steel compounding vessel equipped with a mixer. The drug substance solution is mixed at 250±50 rpm while maintaining the solution temperature between 5°-25° C.

The required quantity of maltose monohydrate powder is added to the compounding vessel. The solution is mixed for a minimum of 10 minutes at 15°-25° C.

The solution pH is adjusted to 7.3-7.7, if necessary using the previously prepared 1 N sodium hydroxide solution or 1 N hydrochloric acid solution. The batch is brought to the final batch weight (final q.s.) using Water for Injection, USP, and mixed for a minimum of 8 minutes. The formulated bulk solution is sampled for pH.

Formulated Bulk Solution is pre-filtered with one 0.45-μm filter. The formulated bulk solution after 0.45-μm filter is sampled for bioburden and bacterial endotoxin (BET).

The pre-filtered formulated bulk Solution is sterile filtered with two 0.22-μm filters in series prior to filling.

Sterile filtered Formulated Bulk Solution is filled and partially stoppered with a 20 nm-Daikyo gray butyl stopper by a fully automatic filling/stoppering machine. The 15-cc Type I flint tubing glass vials are washed and sterilized/depyrogenated.

The filled and partially stoppered drug product vials are lyophilized. A summary of the freeze drying cycle used during lyophilization of abatacept drug product is provided in Table 12 below.

TABLE 12

Freeze dry cycle for abatacept lyophilized drug product

| Process parameter | In-process control |
|---|---|
| Loading Temperature | 5 ± 3° C. |
| Freezing (Shelf Ramp) | From 5° C. to −45° C. in 2.5 hours |
| Freezing | Hold at −45 ± 3° C. for 4 hours |
| Primary Drying (Shelf Ramp) | From −45° C. to −19° C. in 2 hours |
| Primary Drying (Vacuum) | 100 ± 20 microns |
| Primary Drying | Hold at −19 ± 2° C. for 84 hours |
| Intermediate Drying (Shelf Ramp) | From −19° C. to 0° C. in 2 hours |
| Intermediate Drying | Hold at 0 ± 3° C. for 8 hours |
| Secondary Drying (Shelf Ramp) | From 0° C. to 30° C. in 2.5 hours |
| Secondary Drying (Vacuum) | 100 ± 20 microns |
| Secondary Drying | Hold at 30° C. for 12 hours |
| Stoppering | 30 ± 3° C. |
| Stoppering (Vacuum) | 500 ± 100 microns |
| Storage Before Unloading | Hold at 20 ± 3° C. for at least 4 hours |

At the end of the lyophilization cycle, the chamber pressure is raised to 500 microns using sterile filtered nitrogen and vial stoppering is performed under vacuum. The stoppered vials remain inside the lyophilizer for at least 4 hours. The lyophilized and stoppered vials are sealed with a 20-mm aluminum, white flip-off seal under HEPA filtered air by the capping machine. The sealed vials are rinsed with deionized water by an exterior vial washer. The washed drug product vials are stored at 2 to 8° C.

The composition of lyophilized abatacept (250 mg/vial) drug product is listed in Table 13 below.

TABLE 13

Composition of lyophilized abatacept (250 mg/vial) drug product

| Component | Amount (mg/vial)[a] |
|---|---|
| Abatacept | 262.5 |
| Maltose monohydrate | 525 |

TABLE 13-continued

Composition of lyophilized abatacept (250 mg/vial) drug product

| Component | Amount (mg/vial)[a] |
|---|---|
| Sodium phosphate monobasic, monohydrate[b] | 18.1 |
| Sodium chloride[b] | 15.3 |
| Hydrochloric Acid | Adjust to 7.5 |
| Sodium hydroxide | Adjust to 7.5 |

[a]includes a 5% overfill for vial, needle, syringe loss
[b]These components are present in the abatacept drug substance solution

EXAMPLE IV

Belatacept, lyophilized, (100 mg/vial), drug product is a sterile, non-pyrogenic lyophile suitable for intravenous (IV) administration. Each single-use vial contains 100 mg of belatacept with is constituted with 4.2 ml of Sterile Water for Injection, USP to yield a concentration of 25 mg/ml. It can be further diluted to a concentration as low as 1 mg/ml with 5% Dextrose Injection, USP or 0.9% Sodium Chloride Injection, USP at the time of use.

The batch size for drug product manufacture may vary from 20 liters to 120 liters. A representative batch formula for a batch size of 66 liters (12,000 vials) is provided in Table 14 below.

TABLE 14

Batch Formula for a Batch Size of 66 liters (12,000 vials)

| Component | Amount (kg) |
|---|---|
| Belatacept drug substance[a] | 1.32 |
| Sucrose, High Purity, Low Endotoxin | 2.64 |
| Sodium Phosphate Monobasic Monohydrate | 0.18 |
| Sodium Chloride | 0.03 |
| 1N Sodium Hydroxide/or 1N Hydrochloric Acid | Adjust pH to 7.5 |
| Water for Injection | q.s. to batch weight |

[a]Belatacept drug substance: protein concentration 25 mg/ml, 25 mM sodium phosphate, 10 mM sodium chloride, pH of 7.5, <5% HMW species Belatacept lyophilized drug product is manufactured as described in Example III above.

The composition of lyophilized belatacept drug product, 100 mg/vial is listed in Table 15 below.

TABLE 15

Composition of lyophilized belatacept 100 mg/vial drug product

| Component | Amount/Vial (mg) |
|---|---|
| Belatacept | 110[a] |
| Sucrose, High Purity, Low Endotoxin | 220 |
| Sodium Phosphate Monobasic Monohydrate | 15.18 |
| Sodium Chloride | 2.55 |
| 1N Sodium Hydroxide | Adjust to pH 7.5 |
| 1N Hydrochloric Acid | Adjust to pH 7.5 |

[a]Each vial contains 10% overfill for vial, needle and syringe holdup of the reconstituted solution.

EXAMPLE V

Stability studies of the SC liquid formulation of Belatacept drug product were conducted by placing formulations on stability at different temperatures and for various time periods.

Effect of Sucrose

Formulation development studies were conducted to evaluate the effect of various levels of sucrose on solution stability of belatacept drug product. Samples were placed on stability at −70° C., 8° C. and 25° C./60% humidity conditions and monitored at various time points. The ratios of protein to sucrose evaluated were 1:1, 1:1.7 and 1:1.75. The formation of high molecular weight (HMW) species of belatacept was utilized to determine protein stability in solution. Results are shown in Table 16 below.

TABLE 16

Effect of various levels of sucrose on Belatacept drug product at 100 mg/ml

| Storage Condition | Time/ Months | % High Molecular Weight Species | | | |
|---|---|---|---|---|---|
| | | Control[a] | 1:1 | 1:1.75 | 1:1.7 |
| Initial | 0 | 1.11 | 1.07 | 1.05 | 1.06 |
| −70° C. | 3 | 1.18 | 1.09 | 1.07 | 1.09 |
| 8° C. | 1 | 1.22 | 1.10 | 1.08 | 1.07 |
| | 2 | 1.34 | 1.15 | 1.08 | 1.09 |
| | 3 | NA | 1.24 | 1.15 | 1.17 |
| | 6 | 1.78 | 1.39 | 1.23 | 1.24 |
| | 9 | 2.02 | 1.53 | 1.34 | 1.34 |
| | 12 | 2.06 | 1.49 | 1.26 | 1.24 |
| 25° C./60% RH | 0 | 1.11 | 1.07 | 1.05 | 1.06 |
| | 1 | 2.73 | 1.83 | 1.48 | 1.56 |
| | 2 | 3.98 | 2.41 | 1.84 | 1.87 |
| | 3 | 4.88 | 3.02 | NA | 2.23 |
| | 6 | 7.44 | 4.56 | 3.21 | NA |

[a]Belatacept drug product in 10 mM sodium phosphate buffer, 100 mg/ml, pH 7.5

The results of the studies showed that increasing the sucrose to protein ratio improved protein stability. A protein to sucrose ratio of 1:1.36 (wt.:wt.) was chosen for the development of the SC solution because it provided optimum stability without resulting in drug product with excessive hypertonicity.

Effect of Surfactants

The effect of various surfactants in marketed products, such as Polysorbate 80 and Poloxamer 188 on the solution stability of belatacept drug product was evaluated. Poloxamer 188 was evaluated at levels of 4, 6 and 8 mg/ml and Polysorbate 80 was evaluated at 1 and 2 mg/ml of final formulation concentration. Samples were placed on stability at −70° C., 8° C. and 25° C./60% humidity conditions and monitored at various time points. Results are shown in Table 17 below.

TABLE 17

Effect of various levels and types of surfactant on Belatacept drug product (100 mg/ml)

| | | % High Molecular Weight Species | | | | | |
|---|---|---|---|---|---|---|---|
| | Time/ | | Poloxamer 188 mg/ml | | | Polysorbate 80 mg/ml | |
| Storage Condition | Months | Control[a] | 4 | 6 | 8 | 1 | 2 |
| Initial | 0 | 1.11 | 1.06 | 1.07 | 1.07 | 1.08 | 1.08 |
| −70° C. | 3 | 1.18 | 1.09 | NA | 1.09 | 1.11 | 1.15 |
| 8° C. | 1 | 1.22 | 1.10 | 1.08 | 1.09 | 1.10 | 1.12 |
| | 2 | 1.34 | 1.09 | 1.10 | 1.11 | 1.12 | 1.12 |
| | 3 | NA | 1.19 | 1.18 | 1.18 | 1.21 | 1.28 |
| | 6 | 1.78 | 1.27 | 1.23 | 1.25 | 1.29 | 1.30 |
| | 9 | 2.02 | 1.34 | 1.33 | 1.34 | 1.42 | 1.40 |
| | 12 | 2.06 | 1.28 | 1.25 | 1.27 | 1.38 | 1.36 |
| 25° C./60% RH | 0 | 1.11 | 1.06 | 1.07 | 1.07 | 1.08 | 1.08 |
| | 1 | 2.73 | 1.52 | 1.52 | 1.52 | 1.55 | 1.55 |
| | 2 | 3.98 | 1.91 | 1.89 | 1.89 | 1.99 | 1.97 |
| | 3 | 4.88 | 2.31 | 2.29 | 2.24 | 2.56 | 2.50 |
| | 6 | 7.44 | 3.39 | 4.05 | NA | 3.89 | 3.90 |

[a]protein:sucrose (1:1.7), 100 mg/ml, pH 7.5

Results of the effect of surfactants suggested that surfactant did not have a significant effect on the stability of belatacept drug product solution. Among the levels of Poloxamer 188 evaluated, the concentration of 8 mg/ml was found to be adequate to prevent the formation of silicone related particulates in the formulation.

Effect of pH

Stability of the Belatacept SC, (125 mg/ml, protein:sucrose 1:1.36, 8 mg/ml Pluronic F68) drug product was evaluated as a function of pH. The solution pH was adjusted between 7 to 8.2 with either 1N sodium hydroxide or 1N Hydrochloric acid. Samples were placed on stability at 2-8° C. and 25° C./60% RH conditions and monitored at various time points. Analytical testing included pH and SE-HPLC to monitor increase in high molecular weight (HMW) species. These results are summarized in Table 18 below.

TABLE 18

Effect of pH on Belatacept SC drug product*

| | Time/ | % High Molecular Weight Species | | | |
|---|---|---|---|---|---|
| Condition | Months | pH 7.0 | pH 7.4 | pH 7.8 | pH 8.2 |
| Initial | 0 | 1.31 | 1.18 | 1.16 | 1.28 |
| 2-8° C. | 1 | 1.34 | 1.23 | 1.25 | 1.44 |
| | 2 | 1.42 | 1.29 | 3.31 | 1.56 |
| | 3 | 1.48 | 1.35 | 1.36 | 1.59 |
| 25° C./60%RH | 1 | 2.09 | 2.62 | 2.13 | 2.52 |
| | 2 | 7.04 | 5.68 | 5.89 | 6.40 |
| | 3 | 9.98 | 6.13 | NA | 7.81 |

*protein:sucrose (1:1.36), 125 mg/ml, +8 mg/ml Pluronic F68

No significant changes in the rate of formation of HMW species were observed under the recommended storage condition of 2-8° C. Additionally, the solution-state stability data showed the pH of maximum stability to be between 7 and 8. Based on this, a pH range of 7-8 with a target pH of 7.5 was selected for this formulation.

Osmolality

Osmolality of belatacept drug product solutions in various buffers, at different protein concentrations and from separate steps of the formulation process were measured using a vapor pressure method. These results are summarized in Table 19 below.

TABLE 19

Osmolality Determination of Belatacept Drug Product Solution in Various Buffer and Concentration

| Belatacept/Buffer/ Excipients | protein Conc (mg/ml) | Sodium Phosphate | Sodium Chloride | Osmolality (mOsm/kg) |
|---|---|---|---|---|
| Belatacept API, as is | 25 | 25 mM | 10 mM | 89 |
| Belatacept, Diafiltration step | 25 | 10 mM | — | 40 |
| Belatacept Diafiltration/ Concentration step | 138 | 10 mM | — | 58 |
| Belatacept in water | 25 | — | — | 17 |
| Belatacept in water | 100 | — | — | 27 |
| Belatacept:Sucrose (1:1) | 100 | 10 mM | — | 424 |
| Belatacept:Sucrose (1:1.7) | 100 | 10 mM | — | 737 |
| Belatacept:Sucrose (1:1.75) | 100 | 10 mM | — | 769 |
| Belatacept:Sucrose (1:2) | 100 | 10 mM | — | 870 |
| Belatacept:Sucrose (1:1.36) | 125 | 10 mM | — | 770 |

Effect of Agitation/Shaking

The effect of agitation on solution stability of belatacept SC drug product at 100 mg/ml and 125 mg/ml concentration was determined. Aliquots of the solution containing approximately 1 ml in 5 cc tubing vials were shaken at speed 3 of wrist arm shaker at 2-8° C. The temperature of the shaker was maintained at 2-8° C. by placing the shaker in the cold room. Samples were withdrawn at appropriate time intervals and assayed for pH and visual appearance, and same time samples were also evaluated for bioactivity after 30 days of agitation.

Samples agitated at 100 mg/ml and 125 mg/ml concentration for up to 30 days show no change in the level of HMW species, in SDS-PAGE profile, peptide mapping, B7 binding assay, pH, appearance or protein concentration when agitated at 2-8° C.

Effect of Multiple Freeze/Thaw

The effect of multiple freezing and thawing on stability of belatacept SC drug product formulation was investigated in samples with pH ranging from 7.0 to 8.2. Approximately 10 µl aliquots of belatacept SC drug product formulation (125 mg/ml) at pH 7.0, 7.4, 7.8 and 8.2 were dispensed into 30 ml Nalgene PETG containers. Multiple freezing and thawing were performed by storing vials at −70° C. followed by thawing at ambient temperature (25° C.) for 10 minutes. This cycle was repeated for 5 days. The contents of vials were analyzed for pH, % HMW species and appearance after each freeze/thaw cycle.

No change in pH, appearance or % high molecular weight species content was observed in samples during five freeze/thaw cycles.

Recommended Storage Conditions

The recommended storage condition for Belatacept SC drug product, 100 mg/vial (125 mg/ml) is 2-8° C. with a recommended shelf life of 12 months.

Syringe-Ability Study

Syringe-ability study was performed with belatacept SC drug product (125 mg/ml) at 2°-8° C. condition. Various needle sizes with 1 ml and 0.5 mL syringe were evaluated. Syringe filling time and delivery force are recorded in Table 20 below.

TABLE 20

Belatacept SC drug product, 125 mg/ml Syringeability Study at 2°-8° C.

| Syringe Size | Needle size | Filling Time (Sec) | Delivery Force |
| --- | --- | --- | --- |
| 1 mL | 27G ½" | 25 | Moderate |
| 1 mL staked needle(Insulin) | 28G ½" | 52 | Moderate |
| 1 mL staked needle(Insulin) | 29G ½" | 50 | Moderate |
| 0.5 mL staked needle(Insulin) | 30G | 42 (94 for 1 mL) | High |

Based on the syringe-ability study results shown in Table 20. A 21 gauge×1½ inch sterile hypodermic needle is recommended for withdrawal of this product from vial and a 27 gauge×½ inch needle for subsequent dosing.

EXAMPLE VI

Stability studies of the lyophilized formulation of Abatacept drug product were conducted by placing formulations on stability at different temperatures and for various time periods.

Effect of Maltose

Formulation development studies were conducted to evaluate the effect of various levels of maltose on the stability of abatacept drug product. Samples were placed on stability at 50° C. and monitored at various time points. The ratios of protein to maltose evaluated were 1:1, 1:2 and 1:5. The formation of high molecular weight (HMW) species of abatacept was utilized to determine protein stability in solid state. Results are shown in Table 21 below.

TABLE 21

Effect of Maltose on the Freeze-Dried Solid-State Stability of Abatacept drug product at 50° C.

| | Level of High Molecular Weight Species by SE-HPLC (Area %) | | | |
| --- | --- | --- | --- | --- |
| | | Drug to Maltose Weight Ratio | | |
| Time (Weeks) | Without Maltose | 1:1 | 1:2 | 1:5[a] |
| Initial | 0.9 | 0.7 | 0.6 | 2.0 |
| 2 | 5.4 | 3.7 | 2.0 | NA |
| 4 | 8.0 | 5.9 | 2.7 | 2.4 |
| 6 | 10.2 | 6.8 | 3.3 | NA |
| 8 | 11.7 | 7.5 | 3.9 | 2.9 |

[a]Stability of drug product with 1:5 drug-to-maltose weight ratio was evaluated during early development with 50 mg/vial strength. The drug substance lot used in this study was different from that used for other results in this table. This is the reason for the different initial levels of high molecular weight species in these samples.

The results demonstrate that the stability of abatacept drug product in a freeze-dried solid-state form is enhanced in the presence of maltose. Additionally, the minimum amount of maltose useful for stabilization of abatacept was determined to be at a 1:2 protein to maltose weight ratio.

Effect of pH

Stability of lyophilized Abatacept drug product, (250 mg/vial, protein:maltose 1:2) was evaluated as a function of pH. The solution pH was adjusted between 6 to 8 with either 1N sodium hydroxide or 1N Hydrochloric acid. Samples were placed on stability at 2°-8° C. conditions and monitored at various time points. Analytical testing included pH and SE-HPLC to monitor increase in high molecular weight (HMW) species. These results are summarized in Table 22 below.

TABLE 22

Effect of pH on the Rate of Formation of High Molecular Weight (HMW) Species

| | HMW Species Level (Area %) by SE-HPLC at Various pH Values | | | | |
| --- | --- | --- | --- | --- | --- |
| Time (months) | 6.0[a] | 6.5[a] | 7.0 | 7.5 | 8.0 |
| Initial | 0.6 | 0.6 | 2.0 | 2.0 | 2.0 |
| 1 | 0.5 | 0.6 | 2.0 | 2.0 | 2.0 |
| 2 | 0.7 | 0.7 | 2.0 | 2.0 | 2.0 |
| 3 | 0.7 | 0.7 | 2.1 | 2.1 | 2.1 |
| 6 | NA | NA | 1.8 | 1.7 | 1.8 |
| 12 | 0.8 | 0.8 | 1.9 | 1.8 | 1.9 |

[a]The drug substance lot used for pH 6.0 and 6.5 samples was different from that used for pH 7.0, 7.5 and 8.0 samples. This is the reason for the different initial levels of high molecular weight species in these samples.

Under the recommended storage condition of 2°-8° C., no significant changes in the rate of formation of HMW species were observed. Additionally; the solution-state stability data generated during an early development showed the pH of maximum stability to be between 7 and 8.

EXAMPLE VII

Stability studies of the liquid formulation of belatacept (20 mg/ml) drug product were conducted by placing formulations on stability at different temperatures and for various time periods.

Effect of Sucrose

The formulation development studies were conducted to evaluate the effect of various levels of sucrose on the solution stability of belatacept liquid drug product at 20 mg/ml. Samples were placed on stability at 8° C., 25° C./60% humidity and 30° C./60% humidity conditions and monitored at various time points. The ratios of protein to sucrose evaluated were 1:1, 1:2, 1:5 and 1:10 protein:sucrose ratio with 20 mg/mL of belatacept. The formation of high molecular weight (HMW) species of belatacept was utilized to determine protein stability in solution. Results of these study is summarized and shown in Table 23 below.

TABLE 23

Effect of various levels of sucrose on liquid belatacept drug product, 20 mg/ml

| Condition | Time/ Months | % High Molecular Weight Species | | | |
|---|---|---|---|---|---|
| | | 1:1 | 1:2 | 1:5 | 1:10 |
| Initial | 0 | 0.37 | 0.37 | 0.39 | 0.37 |
| 8° C. | 1 | 0.39 | 0.39 | 0.38 | 0.36 |
| | 2 | 0.40 | 0.41 | 0.38 | 0.37 |
| | 3 | 0.43 | 0.39 | 0.36 | 0.36 |
| | 4 | 0.44 | 0.42 | 0.40 | 0.37 |
| | 6 | 0.58 | 0.47 | 0.41 | 0.39 |
| | 9 | 0.54 | 0.45 | 0.42 | 0.39 |
| | 12 | 0.52 | 0.45 | 0.44 | 0.51 |
| 25° C./60% RH | 1 | 0.61 | 0.62 | 0.66 | 0.50 |
| | 2 | 1.25 | 0.99 | 0.58 | 0.53 |
| | 3 | 1.40 | 1.00 | 0.80 | 0.57 |
| | 4 | 1.72 | 1.40 | 1.10 | 0.74 |
| | 6 | 4.29 | 2.70 | 2.09 | 1.18 |
| | 9 | —* | 5.59 | 4.15 | 2.33 |
| 30° C./60% RH | 0.5 | 1.13 | 0.91 | 0.75 | 0.54 |
| | 1 | 1.77 | 2.03 | 1.25 | 0.84 |
| | 2 | 3.01 | 2.90 | 1.78 | 1.10 |
| | 3 | 4.32 | 11.24 | 5.55 | 1.75 |

*Samples not available for analysis due to evaporation

The results of the studies showed that increasing the sucrose to protein ratio improved protein stability. A protein to sucrose ratio of 1:2 (wt.:wt.) was chosen for the development of the liquid solution because it provided optimum stability without resulting in drug product with excessive hypertonicity.

Stability Study

Three liquid beleatacept batches were prepared and placed on stability at 2-8° C. and 25° C./60% RH conditions and monitored at various time points. The weight ratio of protein to sucrose was 1:2. The formation of high molecular weight (HMW) species of belatacept was utilized to determine protein stability in liquid formulation. Stability data is summarized in Table 24 below.

TABLE 24

Stability of liquid belatacept drug product

| Condition | Time Months | Belatacept drug substance (25 mg/mL) Control | Protein:Sucrose (1:2), 20 mg/mL pH 7.5 % HMW species | | |
|---|---|---|---|---|---|
| | | | Batch 1 | Batch 2 | Batch 3 |
| Initial | 0 | 0.40 | 0.37 | 0.43 | 0.91 |
| 5° C. | 1 | 0.44 | 0.39 | 0.45 | 0.90 |
| | 2 | 0.47 | 0.41 | 0.46 | 0.90 |
| | 3 | 0.47 | 0.39 | 0.62 | 0.91 |
| | 4 | 0.54 | 0.42 | NA | 0.92 |
| | 6 | 0.63 | 0.47 | 0.57 | 0.94 |

TABLE 24-continued

Stability of liquid belatacept drug product

| Condition | Time Months | Belatacept drug substance (25 mg/mL) Control | Protein:Sucrose (1:2), 20 mg/mL pH 7.5 % HMW species | | |
|---|---|---|---|---|---|
| | | | Batch 1 | Batch 2 | Batch 3 |
| | 9 | 0.64 | 0.45 | 0.51 | 1.0 |
| | 12 | 0.64 | 0.45 | 0.56 | NA |
| 25° C./60% RH | 1 | 0.61 | 0.62 | 0.60 | 1.04 |
| | 2 | 1.25 | 0.99 | 0.90 | 1.23 |
| | 3 | 1.40 | 1.00 | 1.18 | 1.53 |
| | 4 | 1.72 | 1.40 | 1.60 | 1.79 |
| | 6 | 4.29 | 2.70 | 3.09 | 2.44 |

The data indicate only 0.1% increase in high molecular weight species in liquid formulation compared to 0.2% increase in Belatacept drug substance without sucrose in 12 months at 2-8° C. These results also indicate that addition of sucrose does help in reducing formation of high molecular weight species.

EXAMPLE VIII

Stability studies of the SC formulation of Abatacept drug product were conducted by placing formulations on stability at different temperatures and for various time periods.

Effect of Buffer Strength

Stability of SC Abatacept drug product, (100 mg/ml) was evaluated as a function of buffer strength. The buffer system was either 5 or 10 mM phosphate buffer. Samples were placed on stability at 2-8° C. and 30° C./60% RH conditions and monitored at various time points. Analytical testing included pH and SE-HPLC to monitor increase in high molecular weight (HMW) species. These results are summarized in Table 25 below.

TABLE 25

Effect of buffer strength on Abatacept drug product(100 mg/ml, pH 7.5)

| Storage Condition | Time/ Months | % High Molecular Weight Species | |
|---|---|---|---|
| | | In 10 mM phosphate buffer | In 5 mM phosphate buffer |
| Initial | 0 | 1.30 | 1.47 |
| 2-8° C. | 1 | 1.49 | 1.74 |
| | 2 | 1.60 | 1.98 |
| | 3 | 1.73 | 2.23 |
| 30° C./60% RH | 0 | 1.30 | 1.47 |
| | 0.5 | 8.73 | 14.39 |
| | 1 | 14.63 | 23.24 |
| | 2 | 25.26 | 32.25 |

Stability of the abatacept SC drug product was better in 10 mM phosphate buffer compared to 5 mM phosphate buffer at pH 7.5 at 100 mg/mL abatacept concentration. Moreover the higher buffering capacity of 10 mM phosphate buffer offered better pH control of the formulation compared to 5 mM buffer. Based on the data, 10 mM phosphate buffer was selected for formulation development.

Effect of Sugars

Formulation development studies were conducted to evaluate the effect of various sugars on solution stability of abatacept SC drug product. Samples were placed on stability at 2-8° C. and 30° C./60% humidity conditions and monitored at various time points. The sugars evaluated were sucrose, trehalose and mannitol. The formation of high molecular weight (HMW) species of abatacept was utilized to determine protein stability in solution. Results are shown in Table 26 below.

TABLE 26

Effect of various sugars on Abatacept
SC drug product at 100 mg/ml, pH 7.5

| Storage Condition | Time/ Months | % High Molecular Weight Species | | | |
|---|---|---|---|---|---|
| | | Control[a] | 1:1 Sucrose | 1:1 Trehalose | 1:1 Mannitol[b] |
| Initial | 0 | 1.30 | 1.18 | 1.20 | 1.20 |
| 2-8° C. | 1 | 1.49 | 1.37 | 1.38 | 1.25 |
| | 2 | 1.60 | 1.40 | 1.41 | 1.26 |
| | 3 | 1.73 | 1.45 | 1.48 | 1.60 |
| | 6 | 2.10 | 1.54 | N/A | N/A |
| | 11.5 | 2.57 | N/A | N/A | N/A |
| 30° C./60% RH | 0 | 1.30 | 1.18 | 1.20 | 1.30 |
| | 0.5 | 8.73 | 4.31 | 4.34 | 3.59 |
| | 1 | 14.63 | 7.20 | 8.09 | 5.72 |
| | 2 | 25.26 | 11.97 | 14.21 | 10.14 |

[a]Abatacept drug product in 10 mM sodium phosphate buffer, 100 mg/ml, pH 7.5.
[b]Mannitol formulation at pH 7.8

The results of the studies showed that all three sugars sucrose, trehalose and mannitol offered better stabilization to abatacept compared to the control without sugar. The results of the studies under accelerated conditions of 30C showed that mannitol offered better stabilization to abatacept compared to sucrose and trehalose. Sucrose was slightly better than trehalose. Under refrigeration, the stabilization by all three sugards was not significantly different. Sucrose was chosen as sugar of choice since mannitol formulation had twice the tonicity of the sucrose formulation. Choosing sucrose for stabilization would allow addition of twice as much sucrose to achieve the same tonicity as mannitol at the same ratio but much greater stabilization against aggregation. A protein:sucrose in ratio of 1:1.36 (wt.:wt.) was chosen for the development of the SC drug product because it provided optimum stability without resulting in a drug product with excessive hypertonicity.

Effect of Sucrose

Formulation development studies were conducted to evaluate the effect of various levels of sucrose on solution stability of abatacept SC drug product. Samples were placed on stability at 2-8° C. and 30° C./60% humidity conditions and monitored at various time points. The ratios of protein to sucrose evaluated were 1:1 and 1:2. The formation of high molecular weight (HMW) species of abatacept was utilized to determine protein stability in solution. Results are shown in Table 27 below.

TABLE 27

Effect of various levels of sucrose on Abatacept
SC drug product at 100 mg/ml, pH 7.5

| Storage Condition | Time/ Months | % High Molecular Weight Species | | |
|---|---|---|---|---|
| | | Control[a] | 1:1 | 1:2 |
| Initial | 0 | 1.30 | 1.18 | 1.17 |
| 2-8° C. | 1 | 1.49 | 1.37 | 1.33 |
| | 2 | 1.60 | 1.40 | 1.21 |
| | 3 | 1.73 | 1.45 | 1.23 |
| | 6 | 2.10 | 1.54 | 1.29 |
| | 11.5 | 2.57 | N/A | N/A |
| 30° C./60% RH | 0 | 1.30 | 1.18 | 1.17 |
| | 0.5 | 8.73 | 4.31 | 2.41 |

TABLE 27-continued

Effect of various levels of sucrose on Abatacept
SC drug product at 100 mg/ml, pH 7.5

| Storage Condition | Time/ Months | % High Molecular Weight Species | | |
|---|---|---|---|---|
| | | Control[a] | 1:1 | 1:2 |
| | 1 | 14.63 | 7.20 | 3.69 |
| | 2 | 25.26 | 11.97 | 6.59 |

[a]Abatacept drug product in 10 mM sodium phosphate buffer, 100 mg/ml, pH 7.5

The results of the studies showed that increasing the sucrose to protein ratio improved protein stability. A protein:sucrose ratio of 1:1.36 (wt.:wt.) was chosen for the development of the RTU solution because it provided optimum stability without resulting in drug product with excessive hypertonicity.

Effect of Surfactants

The effect of various surfactants in marketed products, such as Polysorbate 80 (Tween® 80) and Poloxamer 188 (Pluronic® F68) on the solution stability of abatacept SC drag product was evaluated. Poloxamer 188 was evaluated at levels of 4 and 8 mg/ml and Polysorbate 80 was evaluated at 1 and 2 mg/ml of final formulation concentration. Samples were placed on stability at –2-8° C. and 25° C./60% humidity conditions and monitored at various time points. Results are shown in Table 28 below.

TABLE 28

Effect of various levels and types of surfactant
on abatacept SC drug product at 125 mg/ml

| Storage Condition | Time/ Months | % High Molecular Weight Species | | | | |
|---|---|---|---|---|---|---|
| | | Control[a] | Poloxamer 188 mg/ml | | Polysorbate 80 mg/ml | |
| | | | 4 | 8 | 1 | 2 |
| Initial | 0 | 1.05 | 1.05 | 1.06 | 1.07 | 1.10 |
| 2-8° C. | 1 | 0.98 | 0.99 | 0.99 | 1.01 | 1.02 |
| | 2 | 1.02 | 1.03 | 1.04 | 1.05 | 1.07 |
| | 3 | 1.06 | 1.07 | 1.08 | 1.08 | 1.09 |
| | 6 | 1.23 | 1.27 | 1.28 | 1.25 | 1.32 |
| | 9 | 1.30 | 1.35 | 1.36 | 1.34 | 1.36 |
| 25° C./60% RH | 0 | 1.05 | 1.05 | 1.06 | 1.03 | 1.04 |
| | 1 | 1.92 | 1.94 | 1.92 | 1.97 | 2.02 |
| | 2 | 2.69 | 2.71 | 2.68 | 2.75 | 2.80 |
| | 3 | 3.74 | 3.92 | 3.67 | 3.84 | 3.84 |
| | 5 | 5.12 | 5.16 | 5.03 | 5.05 | 5.03 |

[a]protein:sucrose (1:1), 125 mg/ml, pH 7.8

Results of the effect of surfactants suggested that surfactant did not have a significant negative effect on the stability of abatacept SC drug product. Among the levels of Poloxamer 188 evaluated, the concentration of 8 mg/ml was found to be adequate to prevent the formation of silicone related particulates in the formulation.

Osmolality

Osmolality of abatacept in various buffers, at different protein concentrations and from separate steps of the formulation process were measured using a vapor pressure method. These results are summarized in Table 29 below.

TABLE 29

Osmolality Determination of Abatacept SC Solution
in Various Buffer and Concentration

| Abatacept/Buffer/Excipients | protein Conc (mg/ml) | Sodium Phosphate | Sodium Chloride | Osmolality (mOsm/kg) |
|---|---|---|---|---|
| Abatacept drug substance | 50 | 25 mM | 50 mM | 151 |
| Abatacept, Diafiltration step | 50 | 10 mM | — | 32 |
| Abatacept Diafiltration/Concentration step | 155 | 10 mM | — | 49 |
| 10 mM pH 7.8 phosphate buffer | — | 10 | — | 35 |
| Abatacept in water | 100 | 10 mM | — | 51 |
| Abatacept:Sucrose (1:1) | 100 | 10 mM | — | 567 |
| Abatacept:Sucrose (1:1.75) | 100 | 10 mM | — | 766 |
| Abatacept:Sucrose (1:2) | 100 | 10 mM | — | 913 |
| Abatacept:Sucrose (1:1.36) | 125 | 10 mM | — | 782 |

Effect of Agitation/Shaking

The effect of agitation on solution stability of abatacept SC drag product at 100 mg/ml and 125 mg/ml concentration was determined. Aliquots of the solution containing approximately 1 ml in 5 cc tubing vials were shaken at speed 3 of wrist arm shaker at 2-8° C. The temperature of the shaker was maintained at 2-8° C. by placing the shaker in the cold room. Samples were withdrawn at appropriate time intervals and assayed for pH and visual appearance, and same time samples were also evaluated for bioactivity after 30 days of agitation.

Samples agitated at 100 mg/ml and 125 mg/ml concentration for up to 30 days show no change in the level of HMW species, in SDS-PAGE profile, peptide mapping, B7 binding assay, pH, appearance or protein concentration when agitated at 2-8° C.

Recommended Storage Conditions

The recommended storage condition for abatacept SC drug product, 125 mg/Syringe (125 mg/ml) is 2-8° C. with a recommended shelf life of at least 12 months.

EXAMPLE IX

Deamidation and aggregation are two observed degradation pathways of CTLA4Ig molecules. This protocol outlines a laboratory scale pH stability study designed to evaluate the SC drug product formulation in the pH range of 6.3-7.2, specifically pH 6.3, 6.6, 6.9, 7.2. The purpose of this study is to identify the optimal lower pH formulation that will attain a minimum of 18-months of shelf-life for the CTLA4Ig SC formulations with regards to deamidation and formation of high molecular weight species. The SC drug product formulation utilized in this study is described in Table 30 below.

TABLE 30

SC drug product formulation composition at pH 6.9

| Ingredient | Amount mg/1.0 ml |
|---|---|
| abatacept | 125 |
| Sucrose | 170 |
| Poloxamer 188 | 8 |
| Monobasic sodium phosphate, monohydrate | 0.638 |
| Dibasic sodium phosphate, anhydrous | 0.475 |
| Water for Injection | QS 1.0 mL |

Abatacept SC drug product will be formulated at pH 6.3, 6.6, 6.9, 7.2. The drug product will be formulated with sucrose and poloxamer 188 as described above and the final batch concentration will be adjusted with 10 mM phosphate buffer (pH 6.9). The pH will be titrated down to 6.3 and 6.6, respectively, using 1N HCl. Alternatively, the pH will be titrated up to 6.9, 7.2, and 7.65 with 1N NaOH. The drug product will be filled into 1-mL long Physiolis™ syringes (1.0 ml fill volume) and placed on stability stations at 2-8° C., 15° C., 25° C. at 60% humidity, and 35° C. Samples should be protected from light at all times by covering or inserting into brown light-protective bags.

Drug product stored at 2-8° C. will be sampled at 0, 2, 4, 6, 12 18, 24 months and optionally 9 months. Drug product stored at 15° C. will be sampled at 1, 2, 4, 6 months and optionally 9 months. Drug product stored at 25° C. and 60% humidity will be sampled at 1, 2, 4 and 6 months. Drug product stored at 35° C. will be sampled at 1, 2 and 4 months. Samples stored at 2-8° C. will be tested for appearance (initial and last samples only), pH (initial, 4 month and last samples only), A280 (initial, 4 month and last samples only), size exclusion HPLC, SDS-PAGE, tryptic digest peptide mapping (TPM), Biacore B7 Binding (initial, 4 month and last samples only or as needed) and isoelectric focusing (IEF) (initial and last samples only). Samples stored at 15° C. and 25° C. and 60% humidity will be tested for A280 (initial, 4 months and last samples only), size exclusion HPLC, SDS-PAGE and tryptic digest peptide mapping (TPM). Samples stored at 35° C. will be tested for size exclusion HPLC, SDA-PAGE and tryptic digest peptide mapping (TPM).

Non-Routine testing methods will be used to further characterize stability samples at the initial time point, 4 months, 12 months and at the end of the study. Some of these methods may also be used to test specific samples if a trend or an unexpected result is observed. The non-routine methods include: size exclusion chromatography employing multi-angle light scattering (SEC-MALS), kinetic binding (SPR), Mass Spectrometry, CD, AUC, Differential Scanning calorimeter (DSC), FFF, FTIR, size exclusion HPLC (denatured) and SDS-PAGE (silver stain).

EXAMPLE X

A PK substudy was incorporated in a phase 2B, multi-center, randomized, double-blind, placebo-controlled study to evaluate the safety and clinical efficacy of two different doses of abatacept administered intravenously to subjects with active rheumatoid arthritis while receiving methotrexate. In this parallel design study, subjects received abatacept at 2 different doses (2 and 10 mg/kg) or placebo in combination with MTX. Abatacept was manufactured as described in co-pending U.S. patent application Ser. No. 60/752,267, filled on Dec. 20, 2005 which teaches processes for the production of proteins of the invention, specifically recombinant glycoprotein products, by animal or mammalian cell cultures, and supplied in lyophilized form, as described herein, in individual vials containing 200 mg of abatacept. Abatacept was administered IV to subjects on Days 1, 15, and 30, and every 30 days thereafter for a year. Multiple dose PK was derived from the serum concentration vs time data obtained during the dosing interval between Days 60 and 90 from subjects who were enrolled into a site-specific PK substudy. For the subjects in the PK substudy, blood samples were collected before dosing on Day 60, and for a PK profile beginning on Day 60 at 30 minutes (corresponding to the end of abatacept infusion), at 4 hours after the start of infusion, and weekly thereafter until Day 90. A total of 90 subjects were enrolled to participate in the PK substudy. However, complete PK profiles between the dosing interval from Day 60 to 90 were obtained from 29 subjects (15 subjects dosed at 2 mg/kg; 14 subjects dosed at 10 mg/kg).

A summary of the PK parameters is presented in Table 31. The results from the study showed that both Cmax and AUC (TAU), where TAU=30 days, increased in a dose proportional manner. For nominal doses increasing in the ratio of 1:5, the geometric means of Cmax increased in the ratio of 1:5.2, while the geometric mean for AUC(TAU) increased in the ratio of 1:5.0. In addition, T-HALF, CLT, and Vss values appeared to be independent of dose. In these RA subjects, the mean T-HALF, CLT, and Vss values were around 13 days, ~0.2 mL/h/kg, and ~0.07 L/kg, respectively. The small Vss indicates that abatacept is confined primarily to the extracellular fluid volume. Based on the dosing schema of dosing at 2 and 4 weeks after the first infusion, then once a month thereafter, steady-state conditions for abatacept were reached by the third monthly dose. Also, as a result of the dosing schema, serum concentrations were above steady-state trough concentrations during the first 2 months of treatment. Comparison of the trough (Cmin) values at Days 60, 90, and 180 indicated that abatacept does not appear to accumulate following monthly dosing. The mean Cmin steady-state values for all subjects receiving monthly IV doses of 2 and 10 mg/kg abatacept ranged between 4.4 to 6.7 mcg/mL and 22.0 to 28.7 mcg/mL, respectively.

abatacept showed proportional increases of C and AUC over the dose range of 2 mg/kg to 10 mg/kg. At 10 mg/kg, serum concentration appeared to reach a steady-state by day 60 with a mean (range) trough concentration of 24 (1-66) mcg/mL. No systemic accumulation of abatacept occurred upon continued repeated treatment with 10 mg/kg at monthly intervals in RA patients.

Population pharmacokinetic analyses in RA patients revealed that there was a trend toward higher clearance of abatacept with increasing body weight. Age and gender (when corrected for body weight) did not affect clearance. Concomitant methotrexate (MTX), nonsteroidal anti-inflammatory drugs (NSAIDs), corticosteroids, and TNF blocking agents did not influence abatacept clearance.

Serum Assay for Abatacept

Serum samples were analyzed for abatacept by an enzyme-linked immunosorbent assay (ELISA) in a total of 25 analytical runs. All analytical results met the acceptance criteria established prior to sample analysis indicating that the ELISA method was precise and accurate for the quantitation of abatacept in study samples. A summary of the standard curve parameters and mean QC data for abatacept in serum are presented in Table 33. The between- and within-run variabil-

TABLE 31

Summary of Multiple PK studies in Rheumatoid Arthritis Subjects

| Study | Product ID | | | | | | Pharmacokinetic Parameters of Abatacept | | | | |
|---|---|---|---|---|---|---|---|---|---|---|---|
| | | | | | | | Geometric Mean; (% CV) | | | Mean (SD) | |
| Protocol (Country) | (Batch/ Lot #) | Study Objective | Study Design | Subjects (M/Fcm) | Age: (Mean, range) | Treatment Dose (mg/kg) | Cmax (µg/mL) | AUC (TAU) (µg · h/mL) | T-HALF (Days) | CLT (mL/h/kg) | Vss (L/kg) |
| IM101100 (USA) PK Substudy Phase II | C00157 C00196 C98283 | Assess the efficacy, safety, multiple dose PK and immunogenic potential of intravenously administered doses of abatacept | Randomized, double-blind, placebo-controlled, multiple dose study, 30-minute IV infusion | 29 (18/11) | 54 (34-83) | 2.0 (N = 15) 10.0 (N = 14) | 54.9 (29) 284.2 (23) | 9573.5 (30) 47624.2 (31) | 13.5 (5.9) 13.1 (5.3) | 0.23 (0.13) 0.22 (0.09) | 0.07 (0.04) 0.07 (0.03) |

The pharmacokinetics of abatacept were studied in healthy adult subjects after a single 10 mg/kg intravenous infusion and in RA patients after multiple 10 mg/kg intravenous infusions (see Table 32).

TABLE 32

Pharmacokinetic Parameters (Mean, Range) in Healthy Subjects and RA Patients After 10 mg/kg Intravenous Infusion(s)

| PK Parameter | Healthy Subjects (After 10 mg/kg Single Dose) n = 13 | RA Patients (After 10 mg/kg Multiple Doses[a]) n = 14 |
|---|---|---|
| Peak Concentration ($C_{max}$) [mcg/mL] | 292 (175-427) | 295 (171-398) |
| Terminal half-life ($t_{1/2}$) [days] | 16.7 (12-23) | 13.1 (8-25) |
| Systemic clearance (CL) [mL/h/kg] | 0.23 (0.16-0.30) | 0.22 (0.13-0.47) |
| Volume of distribution (Vss) [L/kg] | 0.09 (0.06-0.13) | 0.07 (0.02-0.13) |

[a]Multiple intravenous infusions were administered at days 1, 15, 30, and monthly thereafter.

The pharmacokinetics of abatacept in RA patients and healthy subjects appeared to be comparable. In RA patients, after multiple intravenous infusions, the pharmacokinetics of ity of the analytical QCs for abatacept was 4.5% and 3.5% CV, respectively. Mean observed concentrations of the analytical QC samples deviated less than ±8.9% from the nominal values (Table 33).

TABLE 33

Summary of Quality Control Data for the Assay of Abatacept in Human Serum

| | Nominal Conc. | | |
|---|---|---|---|
| | Low (3.000 ng/mL) | Mid (12.500 ng/mL) | High (24.000 ng/mL) |
| Mean Observed Conc. | 2.866 | 13.608 | 24.526 |
| % Dev | -4.5 | 8.9 | 2.2 |
| Between Run Precision (% CV) | 4.5 | 2.8 | 3.0 |
| Within Run Precision (% CV) | 2.4 | 3.5 | 2.9 |
| Total Variation (% CV) | 5.1 | 4.5 | 4.2 |
| n | 75 | 75 | 75 |
| Number of Runs | 25 | 25 | 25 |

EXAMPLE XI

The objectives of this study are to assess the PK of belatacept following a single SC dose in the range of 50 to 150 mg in healthy subjects; to assess the effects of the injection volume and concentration of the injected solution on the PK of subcutaneously administered belatacept; to assess the safety and tolerability (including the site of injection evaluation) of a single SC dose of belatacept; to assess the immunogenicity of subcutaneously administered belatacept.

This is a double-blind, randomized, placebo-controlled, parallel group, single-dose study in healthy subjects. A total of 42 subjects will be randomized to one of 6 treatment groups. Within each group of 7 subjects, subjects will be randomized in a 5:2 ratio on Day 1 to receive a single, SC injection of belatacept or placebo. Subjects will be required to weigh ≤100 kg. The 6 treatment groups are described in Table 34.

TABLE 34

Treatment Groups

| Treatment Group | Dose of belatacept or Placebo | Injectin Volume | Concentration of the Injected Solution |
|---|---|---|---|
| 1 | 50 mg | 0.4 mL | 125 mg/mL |
| 2 | 75 mg | 0.6 mL | 125 mg/mL |
| 3 | 100 mg | 0.8 mL | 125 mg/mL |
| 4 | 150 mg | 1.2 mL | 125 mg/mL |
| 5 | 50 mg | 1.0 mL | 50 mg/mL |
| 6 | 75 mg | 1.0 mL | 75 mg/mL |

Subjects will undergo screening evaluations to determine eligibility within 28 days of dosing on Day 1. Subjects will be admitted to the clinical facility the day prior to dosing (Day −1) for baseline evaluations, including MLR. Subjects will remain in the clinical facility until completion of post-treatment assessments on Day 5, and will return to the clinical facility for each study visit thereafter until discharged from the study.

On Day 1 subjects will be randomized to treatment and will receive a single SC dose of belatacept or placebo, and undergo detailed PK and immunogenicity sampling. All subjects will receive the SC injections in their anterior thigh. Following study drug administration, the Investigator will assess the injection site for signs of local irritation and inflammation.

Physical examinations, vital sign measurements, and clinical laboratory evaluations will be performed at selected times throughout the study. Blood samples will be collected for up to 56 days after study drug administration for PK analysis and assessment of immunogenicity. Subjects will be monitored for AEs throughout the study. Approximately 265 mL of blood will be drawn from each subject during the study.

Dosing and follow-up will occur concurrently for all dose groups. No subject will receive more than a single dose. Subjects who do not complete the study (except those who are discontinued for AEs) may be replaced.

This is a single dose study. Each subject will undergo a screening period which will be a maximum of 28 days prior to the day study drug is administered. Each subject will remain in the study until the last visit, 56 Days (±2 Days) after study drug is administered. The last visit of the last subject undergoing the trial will be considered the end of the study.

Belatacept 100 mg/vial (125 mg/mL), as described herein, and manufactured as described in co-pending U.S. patent application Ser. No. 60/849,543, filled on Oct. 5, 2006 which teaches processes for the production of proteins of the invention, specifically recombinant glycoprotein products, by animal or mammalian cell cultures, is a ready-to-use liquid product provided in a glass vial for withdrawal and administration using a suitable size conventional syringe and needle for SC administration. A sufficient excess of belatacept is incorporated into each vial to account for withdrawal losses so that 0.8 mL of the solution containing 100 mg can be withdrawn for SC administration.

Belatacept Injection, 100 mg/vial (125 mg/mL) is not intended for an IV infusion Healthy subjects as determined by medical history, physical examination, 12-lead electrocardiogram, and clinical laboratory evaluations will be eligible to participate in the study. This study will include men and women. Subjects must be at least 18 years of age and weigh ≤100 kg at the time of randomization. Female subjects must be not nursing, not pregnant and must be using an acceptable method of contraception for at least 1 month before dosing, during the study and for up to 4 weeks after the end of the study. Women of childbearing potential must have a negative serum pregnancy test within 24 hours prior to the dose of study medication. Subjects will be advised on potential risks to a pregnancy. Male subjects must be using an adequate method of contraception during the study and for up to 4 weeks after the end of the study so that the risk of pregnancy to their partner is minimized. See Section 5 for a detailed list of the inclusion and exclusion criteria.

Medications taken within 4 weeks prior to enrollment must be recorded on the CRF. No concomitant medications (prescription, over-the-counter or herbal) are to be administered during study, except for oral contraceptives, unless they are prescribed by the Investigator for treatment of specific clinical events. Any concomitant therapies must be recorded on the CRF.

PK of belatacept following SC injection will be derived from serum concentration versus time data. The single-dose PK parameters to be assessed include:

Cmax Maximum observed serum concentration
Tmax Time of maximum observed serum concentration
AUC(0-T) Area under the serum concentration-time curve from time zero to the time of the last quantifiable concentration
AUC(INF) Area under the serum concentration-time curve from time zero extrapolated to infinite time
Half life Serum half-life
CLT/F Apparent total body clearance
VSS/F Apparent volume of distribution at steady state Individual subject PK parameter values will be derived by non-compartmental methods by a validated PK analysis program, the eToolbox Kinetica program, Innaphase Corp, Philadelphia, Pa. Dose normalized AUC will also be reported.

Serum samples will be collected over time and assayed for the presence of antibody titers to belatacept using two ELISA assays. One assay assesses the response to the whole molecule and the other to the LEA29Y-T portion only.

All subjects who receive study medication will be included in the safety and PD data sets. Subjects who receive placebo in any panel will be pooled into a single placebo treatment group for PD assessments and safety assessments except for the site of injection assessments. All available data from subjects who receive belatacept will be included in the PK data set, and will be included in the summary statistics and statistical analysis.

Baseline is considered Day −1. Frequency distributions of gender and race will be tabulated by treatment (injection volume and dose). Summary statistics for age, body weight, and height will be tabulated by treatment.

All recorded AEs will be listed and tabulated by preferred term, system organ class, and treatment. Vital signs and clinical laboratory test results will be listed and summarized by treatment. Any significant physical examination findings and clinical laboratory results will be listed. Injection site assessments (erythema, heat, swelling, pain and pruritus) will be tabulated by treatment and degree of severity. Placebo subjects will be pooled across dose groups and analyzed independently, as well, for the assessment of site of injection.

Summary statistics will be tabulated for the PK parameters by treatment. Geometric means and coefficients of variation will be presented for Cmax, AUC(0-T), and AUC(INF). Medians, minima, and maxima will be presented for Tmax. Means and standard deviations will be provided for other PK parameters. To assess the dependency on dose after SC administration, scatter plots of Cmax and AUC(INF) versus dose will be provided. Scatter plots of AUC(INF) and Cmax across injection volumes, will be constructed to assess this effect on the PK of belatacept. Also, scatter plots of Cmax and AUC(INF) versus dose for a fixed volume, and Cmax and AUC(INF) versus volume within doses will be provided where applicable.

Summary statistics will be tabulated by treatment and study day for anti-belatacept and anti-LEA29Y-T antibody values and their changes from baseline (Day 1-0 hr). To explore possible associations between immunogenicity and exposure, plots of changes in anti-belatacept and anti-LEA29Y-T antibodies versus belatacept concentrations will be provided.

PK and immunogenicity blood sampling schedules are outlined in Table 35.

TABLE 35

Pharmacokinetic and Immunogenicity Blood Sampling Schedule

| Study Day | Time (Relative to Dosing) hours:min | PK | Immunogenicity |
|---|---|---|---|
| 1 | 00.00 (predose) | X | X[a] |
|  | 01:00 | X |  |
|  | 02:00 | X |  |
|  | 06:00 | X |  |
|  | 12:00 | X |  |
| 2 | 24:00 | X |  |
|  | 36:00 | X |  |
| 3 | 48:00 | X |  |
|  | 60:00 | X |  |
| 4 | 72:00 | X |  |
|  | 84:00 | X |  |
| 5 | 96:00 | X |  |
| 6 | 120:00 | X |  |
| 7 | 144:00 | X |  |
| 8 | 168:00 | X |  |
| 14 |  | X | X |
| 21 |  | X |  |
| 28 |  | X | X |
| 35 |  | X | X |
| 42 |  | X | X |
| 56 |  | X | X |

[a]Day 1 immunogenicity (anti- belatacept antibodies) sample must be drawn prior to administering drug. Samples on Days 28, 35, 42 and 56 can be drawn within ±2 days.

Table 35 above lists the sampling schedule to be followed for the assessment of PK. Blood samples (~3 nit per sample) will be collected into a pre-labeled, red and gray top (SST) Vacutainer tube via direct venipuncture or from a saline lock. If a saline lock system is used for blood collection, approximately 0.5 mL of blood should be withdrawn through the indwelling catheter and be discarded prior to obtaining each PK sample. Once the PK specimen has been obtained, the blood will be allowed to clot in the Vacutainer® tube at room temperature for 15-30 minutes. Following clotting, the sample must be centrifuged for 15 minutes at 1500×g in a refrigerated centrifuge (4° C.). When centrifugation is complete, at least 0.5 mL of serum from each PK sample time point should be removed by pipette and transferred to a prelabeled, screw cap, polypropylene, PK storage and shipping tube. A clean pipette must be used to aliquot serum for each sample time point. The polypropylene tube containing the PK serum sample may be stored frozen at −20° C. or colder for a maximum of one month and then at −70° C., thereafter. The time permitted from sample collection to freezing of the serum is 12 hours. A sensitive, validated enzyme immunoassay (ETA) method will be used to measure concentrations of belatacept in serum.

Table 35 lists the sampling schedule to be followed for the assessment of immunogenicity. Serum samples will be obtained at visits Days 1, 14, 28, 35, 42, and 56. The Day 1 immunogenicity (anti-belatacept) sample should be taken prior to administering study drug. Samples will be assayed for the presence of anti-belatacept and anti-LEA29Y-T antibodies. For each specimen, blood (~3 mL per sample) will be collected into a pre-labeled red and gray top (SST) Vacutainer® tube via direct venipuncture or from a saline lock (indwelling catheter). If a saline lock system is used for blood collection, approximately 0.5 mL of blood should be drawn through the indwelling catheter and be discarded prior to obtaining each immunogenicity sample. Once the specimen has been obtained, the blood will be allowed to clot in the Vacutainer® tube at room temperature for 15-30 minutes. Following clotting, the sample must be centrifuged for 15 minutes at 1500×g in a refrigerated centrifuge (4° C.) When centrifugation is complete, at least 1 mL of serum should be removed by pipette and transferred to a prelabeled, screw cap, polypropylene, serum sample storage and shipping tube. The polypropylene tube containing the serum sample must be stored frozen at −20° C. or colder. Two sensitive, validated enzyme linked immunosorbent assay (ELISA) methods will be used to measure antibody titers to belatacept in serum. One assay assess the antibody titer to the whole molecule and the other to the LEA29Y-T portion only.

EXAMPLE XII

Deamidation, fragmentation and aggregation are observed degradation pathways of LEA29YIg molecules. This protocol outlines an additional laboratory scale pH stability study designed to evaluate the belatacept SC drug product formulation in the pH range of 6.3-7.5. The purpose of this study is to identify the optimal pH formulation that will attain a minimum of 18-months of shelf-life for the belatacept SC formulation.

For this study, belatacept SC product will be formulated at pH 6.3, 6.6, 6.9, 7.2 and 7.5. The belatacept drug substance at ~25 mg/mL will be first concentrated to ~100 mg/mL, then diafiltered into 10 mM phosphate buffer at pH 6.9 followed by second concentration to obtain a drug product intermediate (DPI) at >160 mg/mL. The DPI will be formulated with sucrose and poloxamer 188 and the final batch concentration will be adjusted with 10 mM phosphate buffer (pH 6.9). The formulated bulk will be subdivided into five sub-batches, as outlined in the study design. The pH of the sub-batches will be titrated down to 6.3 and 6.6, respectively, using 1N HCl. The pH of the additional two sub-batches will be titrated up to 6.9, 7.2 and 7.5 with 1N NaOH. The product batches will be filled into 1-mL long Physiolis™. Samples should be protected from light at all times by covering or inserting into brown light-protective bags. The SC drug product formulation utilized in this study is described in Table 36 below.

TABLE 36

SC drug product formulation composition at pH 6.9

| Ingredient | Amount per 1.0 mL (mg) |
|---|---|
| Belatacept | 125 |
| Sucrose | 170 |
| Poloxamer 188 | 8 |
| Monobasic sodium phosphate, monohydrate | 0.638 |
| Dibasic sodium phosphate, anhydrous | 0.475 |
| Water for Injection | QS 1.0 mL |

Drug product stored at 2-8° C. will be sampled at 0, 2, 4, 6, 12 18, 24 months and optionally 9 months. Drug product stored at 15° C. will be sampled at 1, 2, 4, 6 months and optionally 9 months. Drug product stored at 25° C. and 60% humidity will be sampled at 1, 2, 4 and 6 months. Drug product stored at 35° C. will be sampled at 1, 2 and 4 months. Samples stored at 2-8° C. will be tested for appearance (initial and last samples only), pH (initial, 4 month and last samples only), A280 (initial, 4 month and last samples only), size exclusion-HPLC, SDS-PAGE, tryptic digest peptide mapping (TPM), Biacore B7 Binding (initial, 4 month and last samples only or as needed) and isoelectric focusing (IEF) (initial and last samples only). Samples stored at 15° C. and 25° C. with 60% humidity will be tested for A280 (initial, 4 months and last samples only), size exclusion-HPLC, SDS-PAGE and tryptic digest peptide mapping (TPM). Samples stored at 35° C. will be tested for size exclusion-HPLC, SDA-PAGE and tryptic digest peptide mapping (TPM).

Non-Routine testing methods will be used to further characterize stability samples at the initial time point, 4 months, 12 months and at the end of the study. Some of these methods may also be used to test specific samples if a trend or an unexpected result is observed. The non-routine methods include: size exclusion chromatography employing multi-angle light scattering (SEC-MALS), kinetic binding (SPR), Mass Spectrometry, CD, AUC, Differential Scanning calorimeter (DSC), FFF, FTIR, size exclusion-HPLC (denatured) and SDS-PAGE (silver stain).

What is claimed:

1. A method for treating autoimmune disease comprising administering to a subject in need thereof an effective amount of a stable formulation suitable for subcutaneous administration comprising at least 100 mg/ml CTLA4Ig molecules, a sugar selected from the group consisting of sucrose, lactose, maltose, mannitol and trehalose and mixtures thereof and a pharmaceutically acceptable aqueous carrier wherein the formulation has a pH range of from 6 to 8 and a viscosity of from 9 to 20 centipoise, and the weight ratio of sugar:protein is 1.1:1 or higher.

2. The method of claim 1 wherein the autoimmune disease being treated is selected from the group consisting of lupus erythematosus, lupus nephritis Hashimoto's thyroiditis, Graves' disease, pernicious anemia, autoimmune atrophic gastritis, Addison's disease, type I diabetes mellitus, Goodpasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulcerative colitis, Sjogren's syndrome, rheumatic disease rheumatoid arthritis polymyositis, scleroderma, and mixed connective tissue disease.

3. The method of claim 2 wherein the autoimmune disease being treated is rheumatoid arthritis, scleroderma, autoimmune uveitis, Sjogren's syndrome, type I diabetes mellitus or lupus nephritis.

4. A method for treating rheumatoid arthritis comprising administering to a subject in need thereof an effective amount of a stable formulation suitable for subcutaneous administration comprising the CTLA4Ig molecule having the amino acid sequence shown in SEQ ID NO:2 starting at methionine at position 27 or alanine at position 26 and ending at lysine at position 383 or glycine at position 382 in an amount of about 125 mg/ml, sucrose in an amount of about 170 mg/ml, at least one buffering agent, sterile water for injection and a surfactant, wherein the formulation has a pH range of from 6.8 to 7.4.

5. The method of claim 4 wherein the stable formulation suitable for subcutaneous formulation is administered in about 1 ml volume in a pre-filled syringe.

6. A method for treating autoimmune disease comprising administering to a subject in need thereof an effective amount of a stable formulation suitable for subcutaneous administration comprising at least 125 mg/ml CTLA4Ig molecules, a sugar selected from the group consisting of sucrose, lactose, maltose, mannitol and trehalose and mixtures thereof and a pharmaceutically acceptable aqueous carrier, wherein the formulation has a pH range of from 6 to 8 and a viscosity of from 9 to 20 centipoise, and the weight ratio of sugar:protein is 1.1:1 or higher.

7. The method of claim 1 or 6 wherein the sugar is selected from the group connsisting of sucrose, mannitol or trehalose.

8. The method of claim 7 wherein the sugar is sucrose.

9. The method of claim 8 wherein the weight ratio of sucrose:protein is 1.3:1 to 5:1.

10. The method of claim 9 wherein the weight ratio of sucrose:protein is about 1.4:1.

11. The method of claim 8 wherein the pH range is from 6 to 7.8.

12. The method of claim 1 or 6 wherein the CTLA4Ig molecules have the amino acid sequence shown in SEQ ID NO:2 starting at methionine at position 27 or alanine at position 26 and ending at lysine at position 383 or glycine at position 382.

13. The method of claim 1 or 6 wherein the stable formulation suitable for subcutaneous administration comprises the CTLA4Ig molecules in an amount of about 125 mg/ml, sucrose in an amount of about 170 mg/ml, at least one buffering agent, sterile water for injection and optionally a surfactant, wherein the CTLA4Ig molecule has the amino acid sequence shown in SEQ ID NO:2 starting at methionine at position 27 or alanine at position 26 and ending at lysine at position 383 or glycine at position 382.

14. The method of any one of claim 1, 4 or 6 wherein the stable formulation suitable for subcutaneous administration is stable when stored at 2 to 8° C. for at least 12 months.

15. The method of any one of claim 1, 4 or 6 wherein the stable formulation suitable for subcutaneous administration has an osmolality of from 700 mOsm/kgH$_2$O to 800 mOsm/kgH$_2$O.

16. The method of claim 1 or 6, wherein the stable formulation suitable for subcutaneous administration further comprises a surfactant.

17. The method of claim 16, wherein the surfactant is selected from the group consisting of polysorbates, polysorbate 20, polysorbate 80, poloxamers, poloxamer 188, sorbitan esters, sorbitan derivatives, Triton, sodium laurel sulfate, sodium octyl glycoside, lauryl- sulfobetadine, myristyl-sulfobetadine, linoleyl-sulfobetadine, stearyl-sulfobetadine, lauryl-sarcosine, myristyl-sarcosine, linoleyl-sarcosine, stearyl-sarcosine, linoleyl-betaine, myristyl-betaine, cetyl-betaine, lauramidopropyl-betaine, cocamidopropyl-betaine, linoleamidopropyl-betaine, myristamidopropyl-betaine, palmidopropyl-betaine, isostearamidopropyl-betaine, lauroamidopropyl-dimethylamine, myristamidopropyl-dimethylamine, palmidopropyl-dimethylamine, isostearamidopropyl-dimethylamine, sodium methyl cocoyl-taurate, and disodium methyl oleyl-tauratem, polyethylene glycol, polypropyl glycol, and copolymers of ethylene and propylene glycol.

18. The method of claim 17, wherein the surfactant is poloxamer 188.

19. The method of claim 1 or 6, wherein the stable formulation suitable for subcutaneous administration further comprises a buffering agent.

20. The method of claim 19, wherein the buffering agent is selected from the group consisting of dibasic sodium phosphate anhydrous, monobasic sodium phosphate monohydrate, glycinate buffers, carbonate buffers, citrate buffers and combinations thereof.

21. The method of any one of claim 1, 4 or 6, wherein the stable formulation suitable for subcutaneous administration further comprises a preservative.

22. The method of claim 21, wherein the preservative is selected from the group consisting of octadecyldimethylbenzyl ammonium chloride, hexamethonium chloride, benzalkonium chloride, benzethonium chloride, phenol, butyl alcohol, benzyl alcohol, alkyl parabens, methyl paraben, propyl paraben, catechol, resorcinol, cyclohexanol, 3-pentanol, and m-cresol.

23. The method of any one of claim 1, 4 or 6, wherein the percentage of CTLA4Ig high molecular weight species in the stable formulation suitable for subcutaneous administration is less than about 25%.

24. The method of any one of claim 1, 4 or 6, wherein the percentage of CTLA4Ig high molecular weight species in the stable formulation suitable for subcutaneous administration is less than about 15%.

25. The method of any one of claim 1, 4 or 6, wherein the percentage of CTLA4Ig high molecular weight species in the stable formulation suitable for subcutaneous administration is less than about 10%.

26. The method of any one of claim 1, 4 or 6, wherein the percentage of CTLA4Ig high molecular weight species in the stable formulation suitable for subcutaneous administration is less than about 5%.

27. The method of any one of claim 1, 4 or 6, wherein the percentage of CTLA4Ig high molecular weight species in the stable formulation suitable for subcutaneous administration is less than about 3%.

28. The method of any one of claim 1, 4 or 6, wherein the stable formulation suitable for subcutaneous administration is administered to a subject in single or multiple times per day.

29. The method of any one of claim 1, 4 or 6, wherein the stable formulation suitable for subcutaneous administration is administered to a subject weekly.

30. The method of any one of claim 1, 4 or 6, wherein the stable formulation suitable for subcutaneous administration is administered to a subject monthly.

31. The method of any one of claim 1, 4 or 6, wherein the stable formulation suitable for subcutaneous administration is administered to a subject yearly.

32. The method of claim 1 or 6, wherein the autoimmune disease is rheumatoid arthritis.

33. The method of claim 4 or 32, wherein the stable formulation suitable for subcutaneous administration is administered to a subject who is also being treated with an antirheumatic drug.

34. The method of claim 33, wherein the antirheumatic drug is methotrexate.

35. The method of claim 8, wherein the autoimmune disease is rheumatoid arthritis, the stable formulation suitable for subcutaneous administration further comprises a surfactant, and the percentage of CTLA4Ig high molecular weight species in the formulation is less than about 25%.

36. The method of claim 8, wherein the autoimmune disease is rheumatoid arthritis, the stable formulation suitable for subcutaneous administration further comprises poloxamer 188, and the percentage of CTLA4Ig high molecular weight species in the formulation is less than about 25%.

37. The method of claim 8, wherein the autoimmune disease is rheumatoid arthritis, the stable formulation suitable for subcutaneous administration further comprises a surfactant, and the percentage of CTLA4Ig high molecular weight species in the formulation is less than about 15%.

38. The method of claim 8, wherein the autoimmune disease is rheumatoid arthritis, the stable formulation suitable for subcutaneous administration further comprises poloxamer 188, and the percentage of CTLA4Ig high molecular weight species in the formulation is less than about 15%.

39. The method of claim 8, wherein the autoimmune disease is rheumatoid arthritis, the stable formulation suitable for subcutaneous administration further comprises a surfactant, and the percentage of CTLA4Ig high molecular weight species in the formulation is less than about 10%.

40. The method of claim 8, wherein the autoimmune disease is rheumatoid arthritis, the stable formulation suitable for subcutaneous administration further comprises poloxamer 188, and the percentage of CTLA4Ig high molecular weight species in the formulation is less than about 10%.

41. The method of claim 8, wherein the autoimmune disease is rheumatoid arthritis, the stable formulation suitable for subcutaneous administration further comprises a surfactant, and the percentage of CTLA4Ig high molecular weight species in the formulation is less than about 5%.

42. The method of claim 8, wherein the autoimmune disease is rheumatoid arthritis, the stable formulation suitable for subcutaneous administration further comprises poloxamer 188, and the percentage of CTLA4Ig high molecular weight species in the formulation is less than about 5%.

43. The method of claim 8, wherein the autoimmune disease is rheumatoid arthritis, the stable formulation suitable for subcutaneous administration further comprises a surfactant, and the percentage of CTLA4Ig high molecular weight species in the formulation is less than about 3%.

44. The method of claim 8, wherein the autoimmune disease is rheumatoid arthritis, the stable formulation suitable for subcutaneous administration further comprises poloxamer 188, and the percentage of CTLA4Ig high molecular weight species in the formulation is less than about 3%.

* * * * *

SEQUENCE LISTING

<160> NUMBER OF SEQ ID NOS: 4

<210> SEQ ID NO 1
<211> LENGTH: 1152
<212> TYPE: DNA
<213> ORGANISM: Artificial Sequence
<220> FEATURE:
<223> OTHER INFORMATION: CTLA4Ig

<400> SEQUENCE: 1

```
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gcttttgtgtg tgagtatgca tctccaggca aagccactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg gactctacat ctgcaaggtg     360
gagctcatgt acccaccgcc atactacctg ggcataggca acgaaccca gatttatgta     420 attgatccag aaccgtgccc agattctgat caggagccca aatcttctga caaaactcac     480
acatccccac cgtccccagc acctgaactc ctgggtggat cgtcagtctt cctcttcccc     540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg ggtggtcagc     720
gtcctcaccg tcctgcacca ggactggctg aatggcaagg agtacaagtg caaggtctcc     780
aacaaagccc tcccagcccc catcgagaaa accatctcca aagccaaagg gcagccccga     840
gaaccacagg tgtacaccct gcccccatcc cgggatgagc tgaccaagaa ccaggtcagc     900
ctgacctgcc tggtcaaagg cttctatccc agcgacatcg ccgtggagtg ggagagcaat     960
gggcagccgg agaacaacta caagaccacg cctcccgtgc tggactccga cggctccttc    1020
ttcctctaca gcaagctcac cgtggacaag agcaggtggc agcaggggaa cgtcttctca    1080
tgctccgtga tgcatgaggc tctgcacaac cactacacgc agaagagcct ctccctgtct    1140
ccgggtaaat ga                                                        1152
```

```
<210> SEQ ID NO 2
<211> LENGTH: 383
<212> TYPE: PRT
<213> ORGANISM: Artificial Sequence
<220> FEATURE:
<223> OTHER INFORMATION: CTLA4Ig

<400> SEQUENCE: 2

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365
```

His Asn His Tyr Thr Gln Lys Ser Leu Ser Leu Ser Pro Gly Lys
    370                 375                 380

<210> SEQ ID NO 3
<211> LENGTH: 1152
<212> TYPE: DNA
<213> ORGANISM: Artificial Sequence
<220> FEATURE:
<223> OTHER INFORMATION: L104EA29YIg

<400> SEQUENCE: 3

| | |
|---|---:|
| atgggtgtac tgctcacaca gaggacgctg ctcagtctgg tccttgcact cctgtttcca | 60 |
| agcatggcga gcatggcaat gcacgtggcc cagcctgctg tggtactggc agcagccga | 120 |
| ggcatcgcta gctttgtgtg tgagtatgca tctccaggca aatatactga ggtccgggtg | 180 |
| acagtgcttc ggcaggctga cagccaggtg actgaagtct gtgcggcaac ctacatgatg | 240 |
| gggaatgagt tgaccttcct agatgattcc atctgcacgg gcacctccag tggaaatcaa | 300 |
| gtgaacctca ctatccaagg actgagggca atggacacgg gactctacat ctgcaaggtg | 360 |
| gagctcatgt acccaccgcc atactacgag ggcataggca acggaaccca gatttatgta | 420 |
| attgatccag aaccgtgccc agattctgat caggagccca atcttctga caaaactcac | 480 |
| acatccccac cgtccccagc acctgaactc ctggggggat cgtcagtctt cctcttcccc | 540 |
| ccaaaaccca aggacaccct catgatctcc cggacccctg aggtcacatg cgtggtggtg | 600 |
| gacgtgagcc acgaagaccc tgaggtcaag ttcaactggt acgtggacgg cgtggaggtg | 660 |
| cataatgcca agacaaagcc gcgggaggag cagtacaaca gcacgtaccg tgtggtcagc | 720 |
| gtcctcaccg tcctgcacca ggactggctg aatggcaagg agtacaagtg caaggtctcc | 780 |
| aacaaagccc tcccagcccc catcgagaaa accatctcca agccaaagg gcagccccga | 840 |
| gaaccacagg tgtacaccct gcccccatcc cgggatgagc tgaccaagaa ccaggtcagc | 900 |
| ctgacctgcc tggtcaaagg cttctatccc agcgacatcg ccgtggagtg ggagagcaat | 960 |
| gggcagccgg agaacaacta caagaccacg cctcccgtgc tggactccga cggctccttc | 1020 |
| ttcctctaca gcaagctcac cgtggacaag agcaggtggc agcaggggaa cgtcttctca | 1080 |
| tgctccgtga tgcatgaggc tctgcacaac cactacacgc agaagagcct ctccctgtct | 1140 |
| ccgggtaaat ga | 1152 |

<210> SEQ ID NO 4
<211> LENGTH: 383
<212> TYPE: PRT
<213> ORGANISM: Artificial Sequence
<220> FEATURE:
<223> OTHER INFORMATION: L104EA29YIg

<400> SEQUENCE: 4

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
                20                  25                  30

Ala Val Val Leu Ala Ser Ser Arg Gly Ile Ala Ser Phe Val Cys Glu
        35                  40                  45

Tyr Ala Ser Pro Gly Lys Tyr Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser

```
                      85                  90                  95
    Ser Gly Asn Gln Val Asn Leu Thr Ile Gln Gly Leu Arg Ala Met Asp
                100                 105                 110

Thr Gly Leu Tyr Ile Cys Lys Val Glu Leu Met Tyr Pro Pro Pro Tyr
                115                 120                 125

Tyr Glu Gly Ile Gly Asn Gly Thr Gln Ile Tyr Val Ile Asp Pro Glu
                130                 135                 140

Pro Cys Pro Asp Ser Asp Gln Glu Pro Lys Ser Ser Asp Lys Thr His
    145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
                180                 185                 190

Pro Glu Val Thr Cys Val Val Val Asp Val Ser His Glu Asp Pro Glu
                195                 200                 205

Val Lys Phe Asn Trp Tyr Val Asp Gly Val Glu Val His Asn Ala Lys
                210                 215                 220

Thr Lys Pro Arg Glu Glu Gln Tyr Asn Ser Thr Tyr Arg Val Val Ser
    225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
                260                 265                 270

Ser Lys Ala Lys Gly Gln Pro Arg Glu Pro Gln Val Tyr Thr Leu Pro
                275                 280                 285

Pro Ser Arg Asp Glu Leu Thr Lys Asn Gln Val Ser Leu Thr Cys Leu
                290                 295                 300

Val Lys Gly Phe Tyr Pro Ser Asp Ile Ala Val Glu Trp Glu Ser Asn
    305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
                340                 345                 350

Trp Gln Gln Gly Asn Val Phe Ser Cys Ser Val Met His Glu Ala Leu
                355                 360                 365

His Asn His Tyr Thr Gln Lys Ser Leu Ser Leu Ser Pro Gly Lys
    370                 375                 380
```